US010717779B2

(12) United States Patent
Gros et al.

(10) Patent No.: US 10,717,779 B2
(45) Date of Patent: Jul. 21, 2020

(54) METHODS FOR BLOCKING AN INTERACTION BETWEEN NOTCH-1 AND DELTA-LIKE 4 (DLL-4) BY ADMINISTERING A DDL-4 ANTIBODY

(71) Applicant: SORRENTO THERAPEUTICS, INC., San Diego, CA (US)

(72) Inventors: Edwige Gros, San Diego, CA (US); Yanliang Zhang, San Diego, CA (US); Heyue Zhou, San Diego, CA (US); Randy Gastwirt, San Diego, CA (US)

(73) Assignee: Sorrento Therapeutics, San Diego, CA (US)

( * ) Notice: Subject to any disclaimer, the term of this patent is extended or adjusted under 35 U.S.C. 154(b) by 0 days.

(21) Appl. No.: 16/241,828

(22) Filed: Jan. 7, 2019

(65) Prior Publication Data
US 2019/0169282 A1 Jun. 6, 2019

Related U.S. Application Data

(62) Division of application No. 13/903,793, filed on May 28, 2013, now Pat. No. 10,174,107.

(60) Provisional application No. 61/654,019, filed on May 31, 2012.

(51) Int. Cl.
*C07K 16/22* (2006.01)
*C07K 16/28* (2006.01)

(52) U.S. Cl.
CPC .............. *C07K 16/22* (2013.01); *C07K 16/28* (2013.01); *C07K 2317/21* (2013.01); *C07K 2317/76* (2013.01); *C07K 2317/92* (2013.01)

(58) Field of Classification Search
CPC .... C07K 16/22; C07K 16/28; C07K 2317/21; C07K 2317/76; C07K 2317/92
See application file for complete search history.

(56) References Cited

U.S. PATENT DOCUMENTS

| 10,174,107 | B2 | 1/2019 | Gros et al. |
| 2003/0059937 | A1 | 3/2003 | Ruben et al. |
| 2008/0025980 | A1 | 1/2008 | Hardy et al. |
| 2010/0292312 | A1 | 11/2010 | Yan et al. |
| 2011/0117079 | A1 | 5/2011 | Benatuil et al. |

FOREIGN PATENT DOCUMENTS

| WO | WO 2008/042236 A2 | 4/2008 |
| WO | WO 2008/060705 A2 | 5/2008 |
| WO | WO 2008/076379 A2 | 6/2008 |
| WO | WO 2010/032060 A1 | 3/2010 |

OTHER PUBLICATIONS

Adderson et al. "Immunoglobulin light chain variable region gene sequences for human antibodies to Haemophilus influenzae type b capsular polysaccharide are dominated by a limited number of V kappa and V lambda segments and VJ combinations," J. Clin. Invest. 89(3):729-738 (1992).
Chapal et al. "Thyroid Peroxidase Autoantibodies Obtained from Random Single Chain Fv Libraries Contain he Same Heavy/Light Chain Combinations as Occur in Vivo," Endocrinology. 142(11): 4740-4750 (2001).
Colman P. M., "Effects of amino acid sequence changes on antibody-antigen interactions," Research in Immunology, 145: 33-36 (1994).
Combriato et al. "Vλ and Jλ-Cλ gene segments of the human immunoglobulin A. light chain locus are separated by 14 kb and rearrange by a deletion mechanism," Eur. J. Immunol. 21(6)1 513-1522 (1991).
Genbank Database [Online] (Jul. 24, 2016) "immunoglobulin kappa light chain, partial [*Homo sapiens*]," Accession No. BAH04733. National Center for Biotechnology Information. Accessible on the Internet at URL: https:/www.ncbi.rilm.nih.gov/protein/219566443. [Last Accessed Jun. 5, 2017].
Genbank Database [Online] (Jul. 26, 2016) "immunoglobulin heavy chain VHDJ region, partial [*Homo sapiens*]," Accession No. BAC01307. National Center for Biotechnology Information. Accessible on the Internet at URL: https://NWW.ncbi.nlm.nih.gov/protein/BAC01307. [Last Accessed Jun. 5, 2017].
Genbank Database [Online] (Jul. 26, 2016) "immunoglobulin heavy chain VHDJ region, partial [*Homo sapiens*]," Accession No. BAC01540. National Center for Biotechnology Information. Accessible on the Internet at URL: https://NWW.ncbi.nlm.nih.gov/protein/BAC01540. [Last Accessed Jun. 5, 2017].
Genbank Database [Online] (Jul. 26, 2016) "immunoglobulin heavy chain VHDJ region, partial [*Homo sapiens*]," Accession No. BACO2373. National Center for Biotechnology Information. Accessible on the Internet at URL: https://NWW.ncbi.nlm.nih.gov/protein/BACO2373. [Last Accessed Jun. 5, 2017].
Genbank Database [Online] (Jul. 26, 2016) "immunoglobulin lambda light chain VLJ region, partial [*Homo sapiens*)." Accession No. BAC01602. National Center for Biotechnology Information. Accessible on the Internet at URL: https:/lwww.ncbi.nlm.nih.gov/protein/BAC01602. [Last Accessed Jun. 5, 2017].

(Continued)

*Primary Examiner* — Robert S Landsman
(74) *Attorney, Agent, or Firm* — McNeill Baur PLLC

(57) ABSTRACT

There is disclosed compositions and methods relating to or derived from anti-DLL-4 antibodies. More specifically, there is disclosed fully human antibodies that bind DLL-4, DLL-4-binding fragments and derivatives of such antibodies, and DLL-4-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having DLL-4 related disorders or conditions, including various inflammatory disorders and various cancers.

28 Claims, 10 Drawing Sheets
Specification includes a Sequence Listing.

(56) References Cited

OTHER PUBLICATIONS

Genbank Database [Online] (Jul. 26, 2016) "immunoglobulin lambda light chain VLJ region, partial [*Homo sapiens*]." Accession No. BAC01606. National Center for Biotechnology Information. Accessible on the Internet at URL: https:/lwww.ncbi.nlm.nih.gov/protein/BAC01606. [Last Accessed Jun. 5, 2017].

Genbank Database [Online] (Jul. 26, 2016) "immunoglobulin lambda light chain VLJ region, partial [*Homo sapiens*]." Accession No. BAC01631. National Center for Biotechnology Information. Accessible on the Internet at URL: https:/lwww.ncbi.nlm.nih.gov/protein/BAC01631. [Last Accessed Jun. 5, 2017].

International Search Report with Written Opinion corresponding to International Patent Application No. PCT/US2013/042912, dated Jul. 30, 2014.

Jiminez-Gomez et al. "Modulated selection of IGHV gene somatic hypermutation during systemic maturation of human plasma cells," J. Leukoc. Biol. 87(3):523-530 (2010).

Paul, W.E., Fundamental Immunology, 3rd Edition, Raven Press, New York, Chapt. 8, pp. 292-295 (1993).

Rudikoff, et al., "Single amino acid substitution altering antigen-binding specificity," Proc. Natl. Acad. Sci. USA, 79(6):1979-1983 (Mar. 1982).

Shriner et al. "Analysis of the young and elderly variable gene repertoire in response to pneumococcal polysaccharides using a reconstituted SCIO mouse model," Vaccine. 24(49-50):7159-7166 (2006).

Tian et al. "Evidence for preferential Ig gene usage and differential TdT and exonuclease activities in human naïve and memory B cells," Mol Immunol. 44(9):2173-2183 (2007).

Tian et al. "Immunodominance of the VH1-46 Antibody Gene Segment in the Primary Repertoire of Human Rotavirus-Specific B Cells Is Reduced in the Memory Compartment Through Somatic Mutation of Nondominant Clones," J. Immunol. 180(5):3279-3288 (2008).

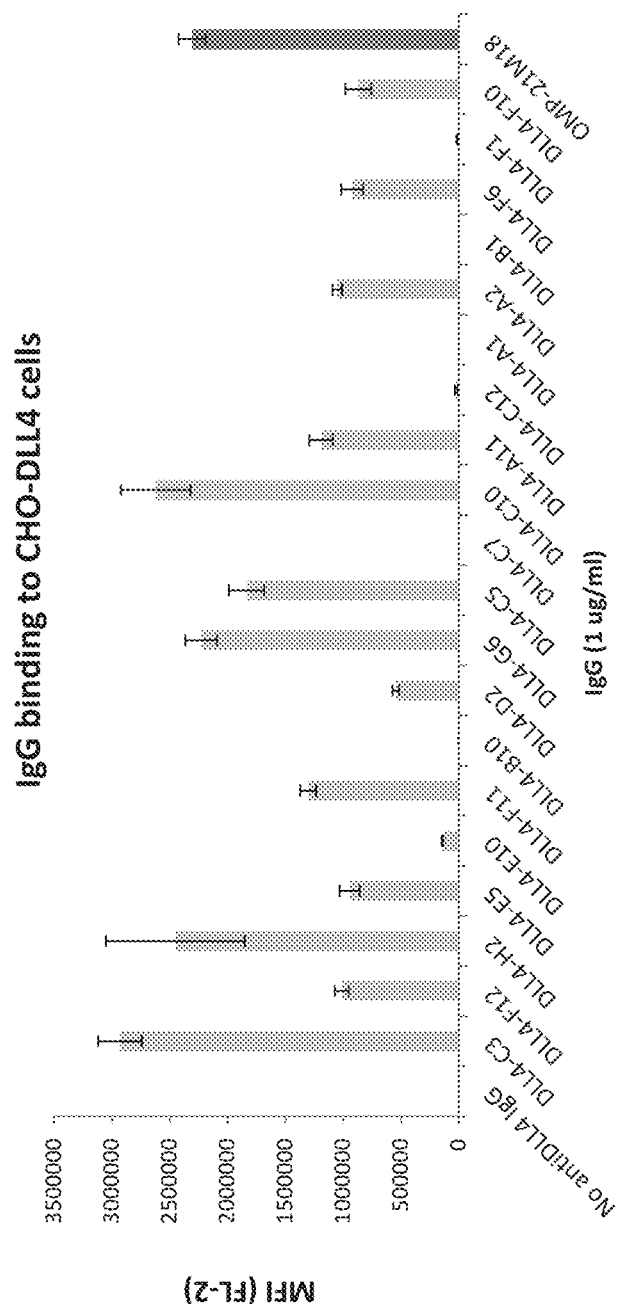
Fig 1A. Binding of various anti-DLL4 antibodies to Cell Surface DLL4 Protein.

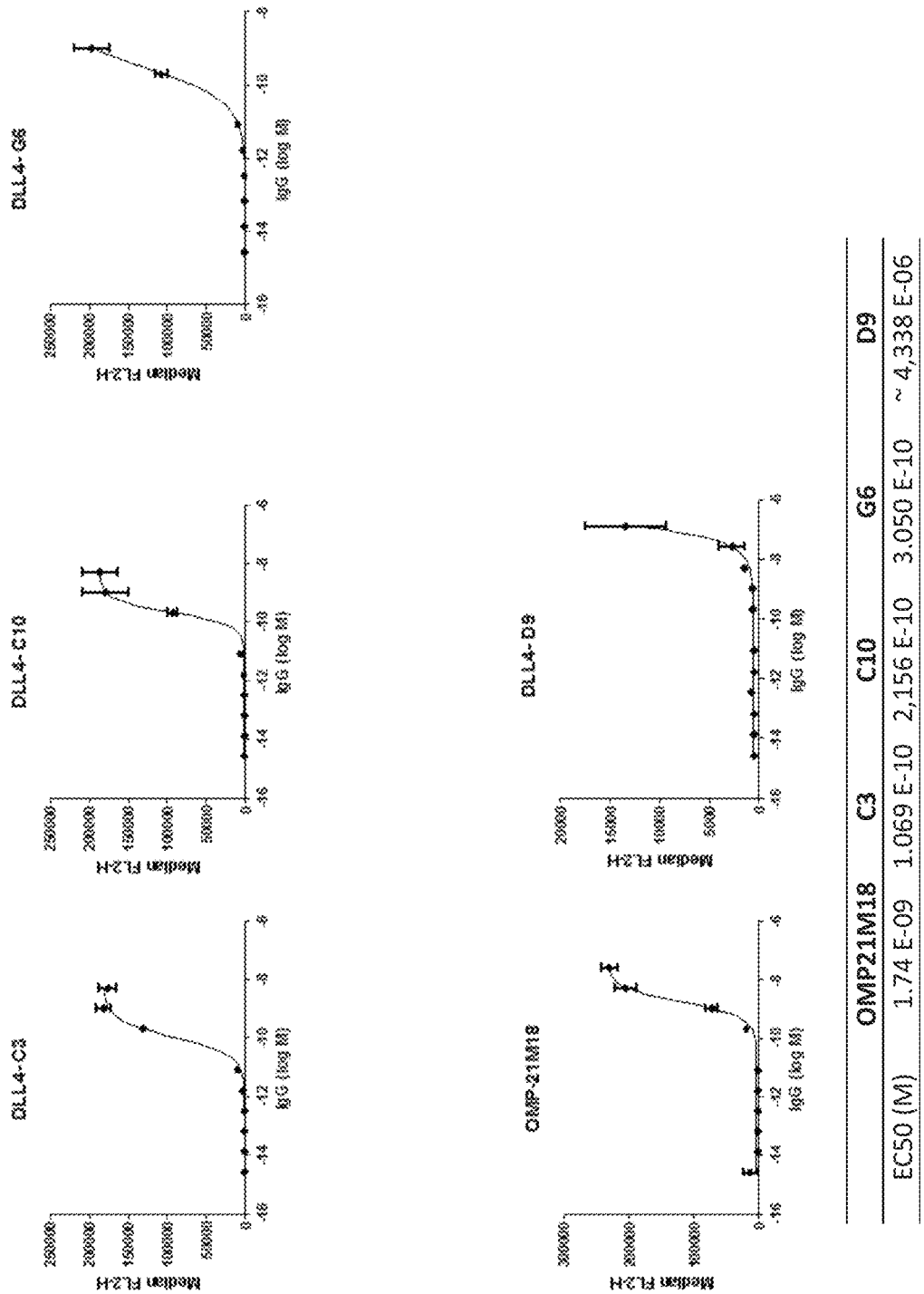
Fig 1B. Binding of selected anti-DLL4 antibodies to Cell Surface DLL4 Protein.

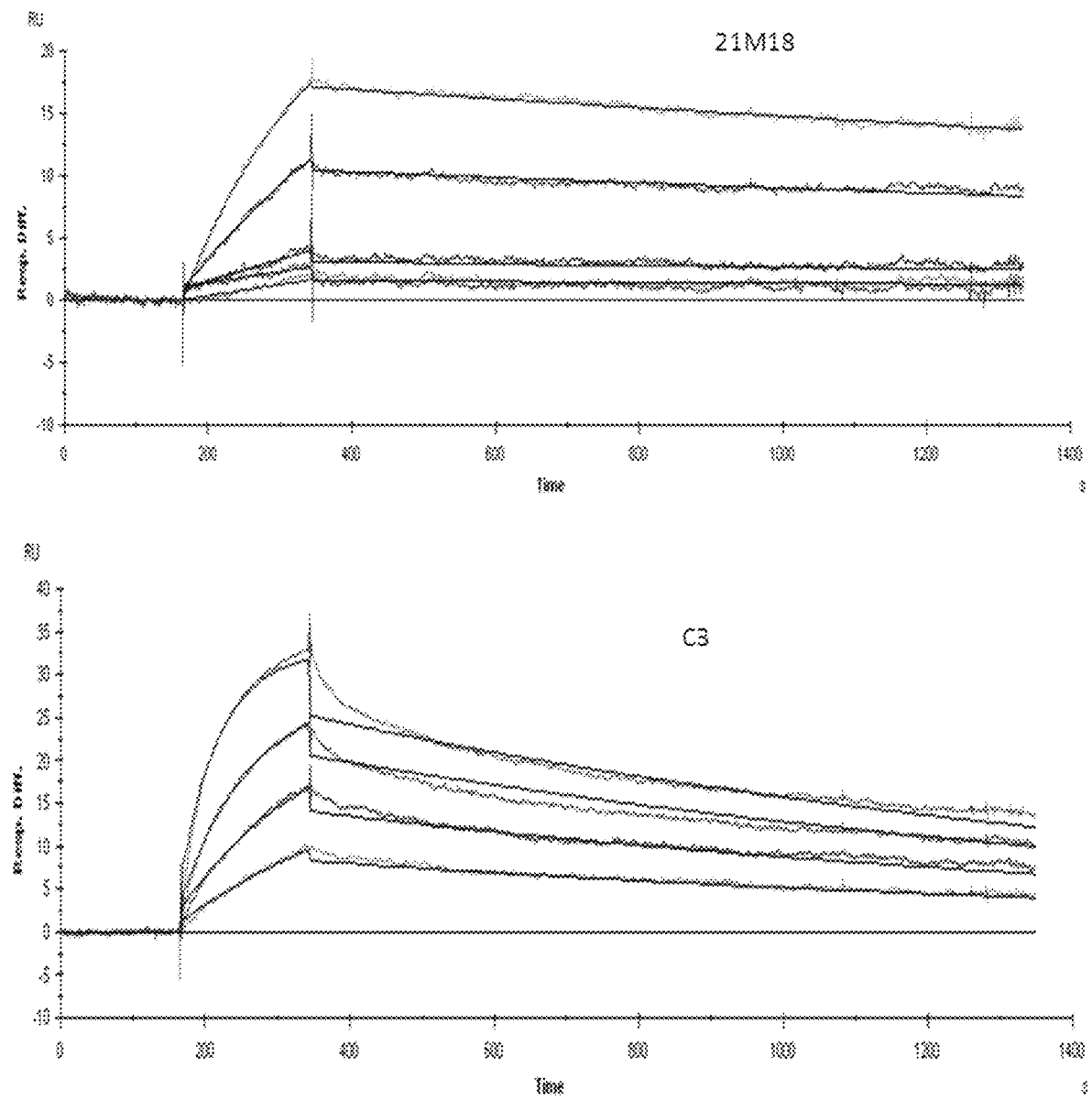
FIG 2 Kinetic Analysis of IgGs Against Recombinant Human DLL4 by Biacore Figure 2 continued
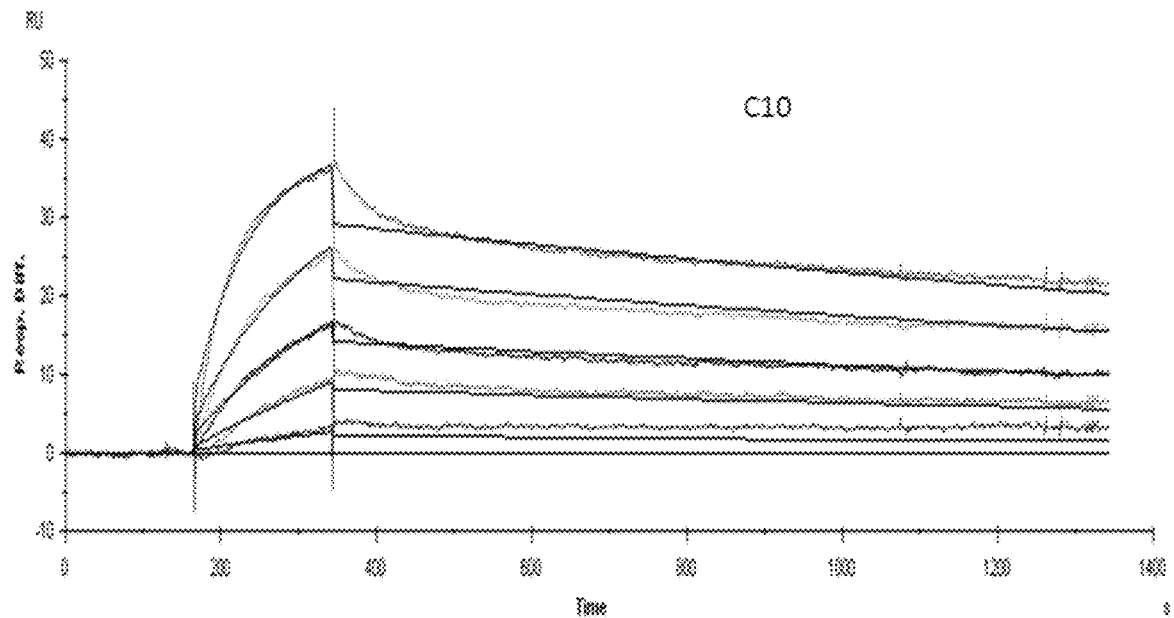
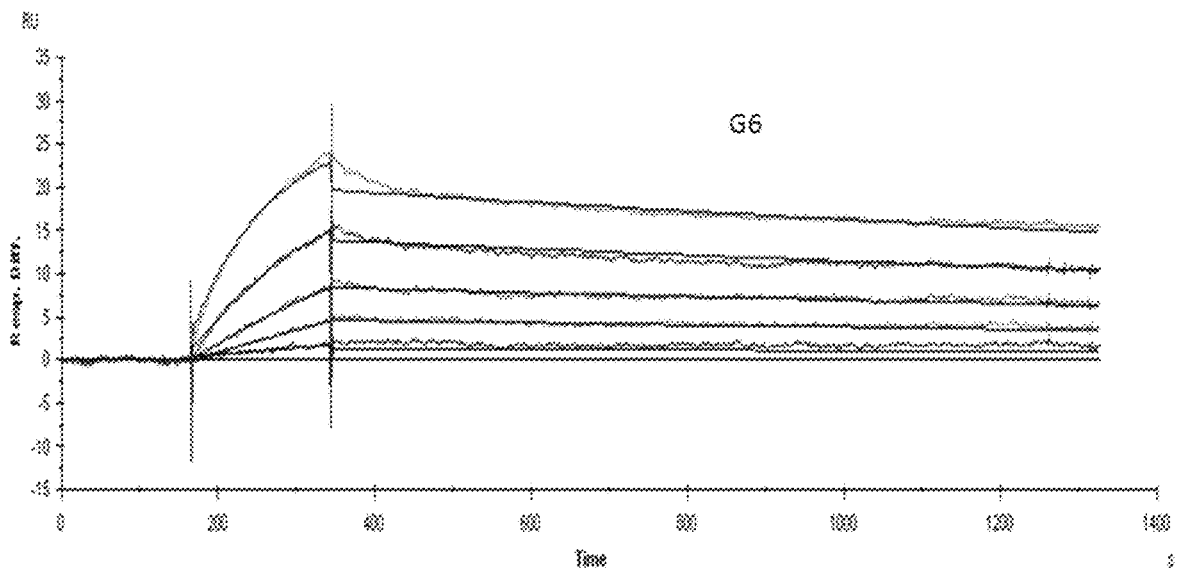
| Name | ka (1/Ms) | kd (1/s) | Rmax (RU) | KA (1/M) | KD (M) | Chi2 |
|---|---|---|---|---|---|---|
| 21M18 | 1.32E+5 | 2.26E-04 | 28.8 | 5.863E+08 | 1.71E-9 | 0.0699 |
| C3 | 8.91E+05 | 7.88E-04 | 27.9 | 1.13E+09 | 8.84E-10 | 0.425 |
| C10 | 3.4E+05 | 4.01E-04 | 33.2 | 8.49E+08 | 1.18E-9 | 0.903 |
| G6 | 2.52E+05 | 2.89E-04 | 24.2 | 8.72+E08 | 1.15E-09 | 0.211 |

Fig 3A - Epitope mapping of STI Anti-DLL4 Antibodies compared to OMP21M18 using Octet
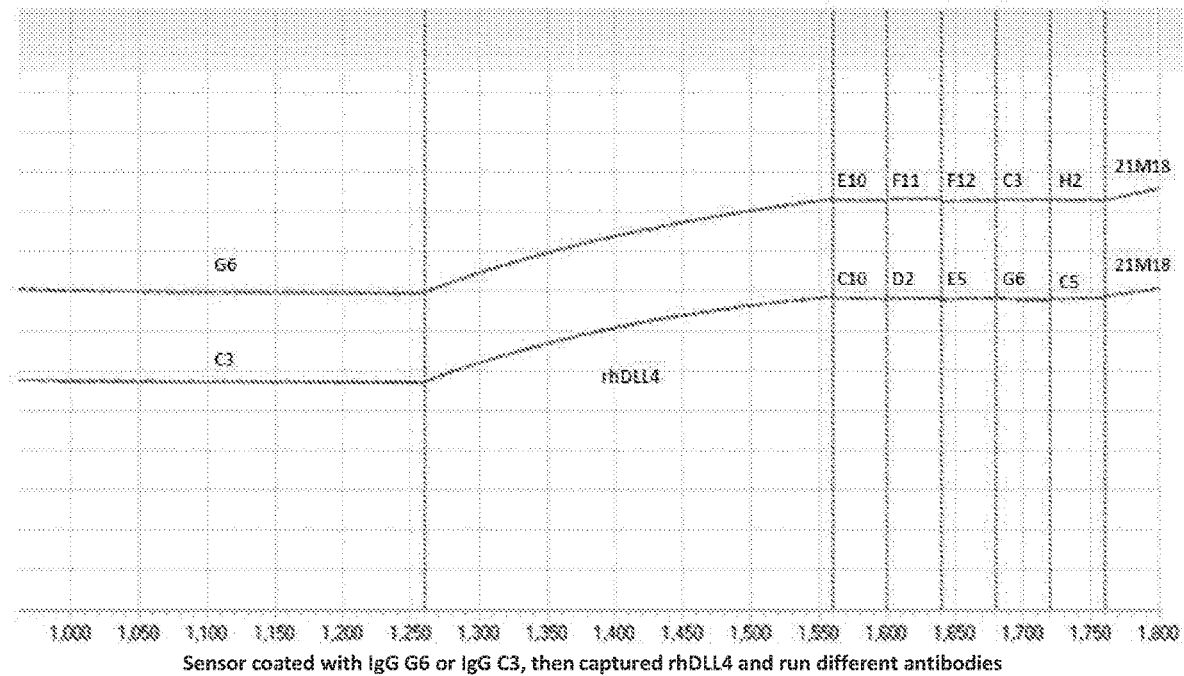
Sensor coated with IgG G6 or IgG C3, then captured rhDLL4 and run different antibodies
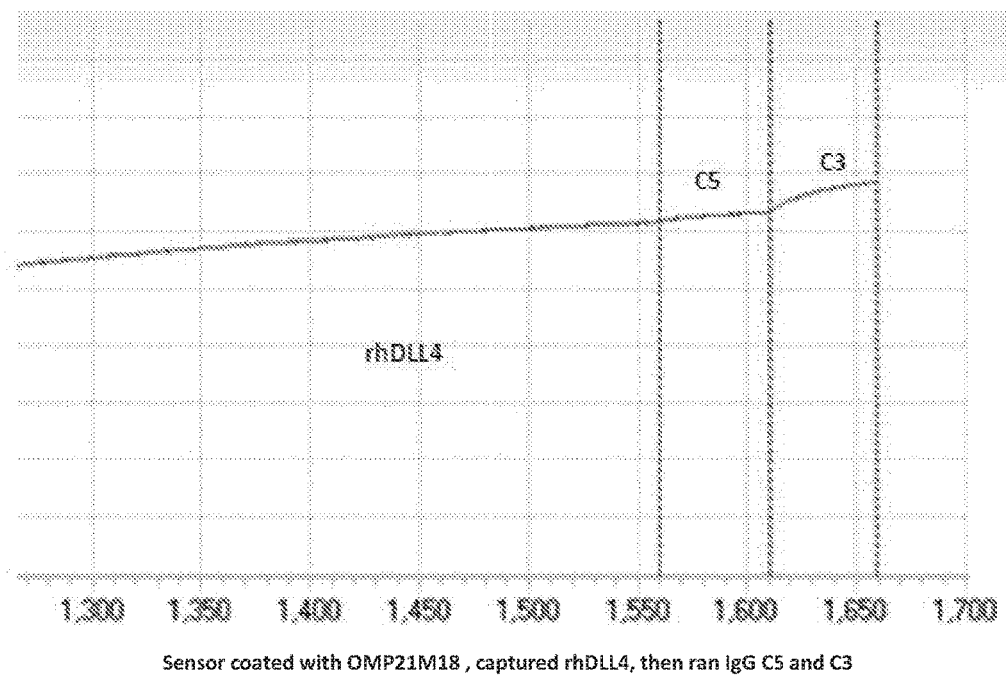
Sensor coated with OMP21M18, captured rhDLL4, then ran IgG C5 and C3
Fig 3B - Epitope mapping of STI Anti-DLL4 Antibodies compared to OMP21M18 using Octet

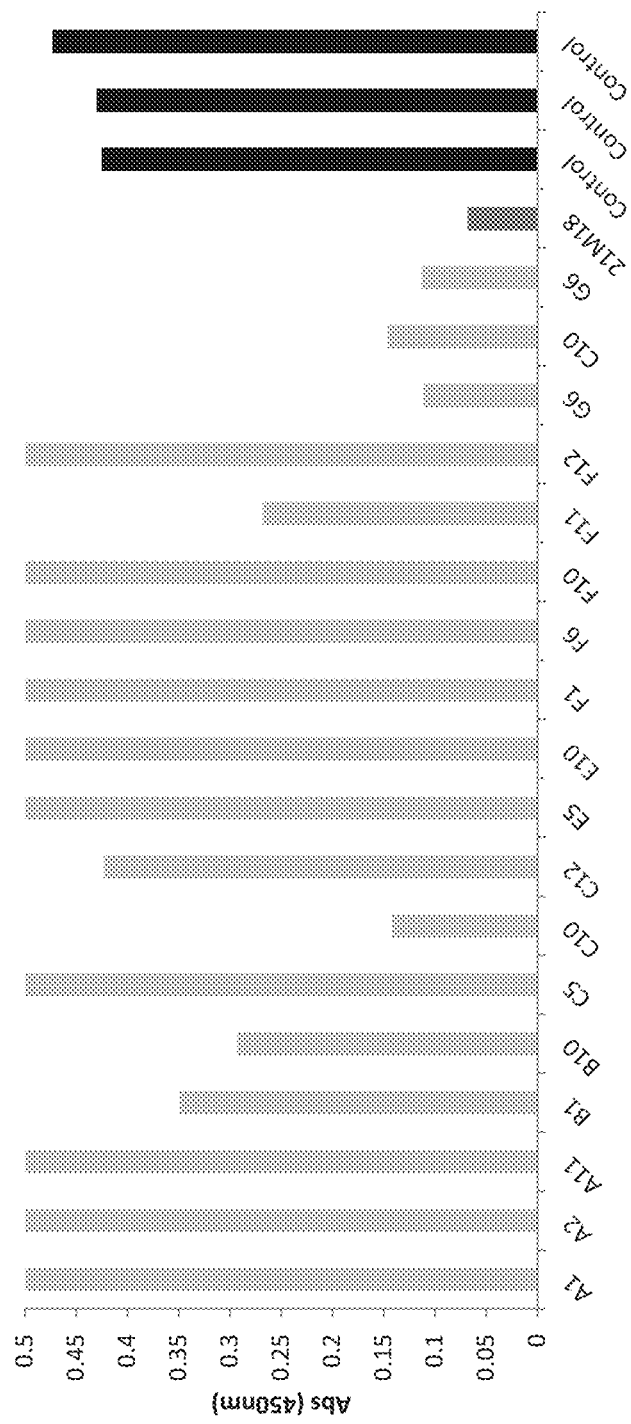

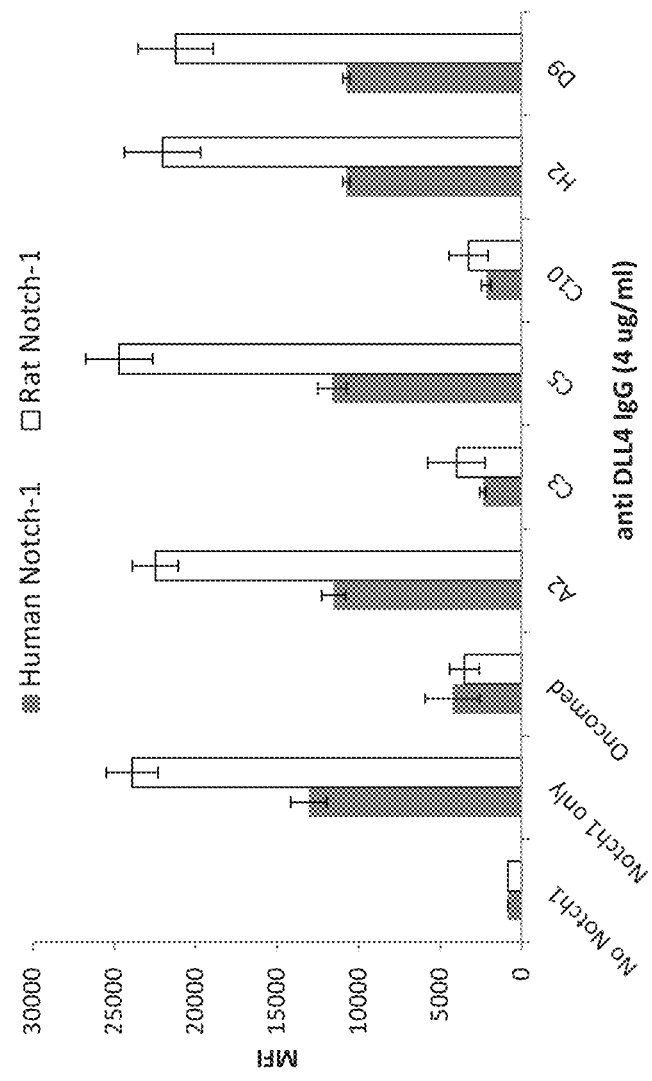
Fig 4B. Inhibition of human or rat soluble Notch-1 to Cellular DLL4

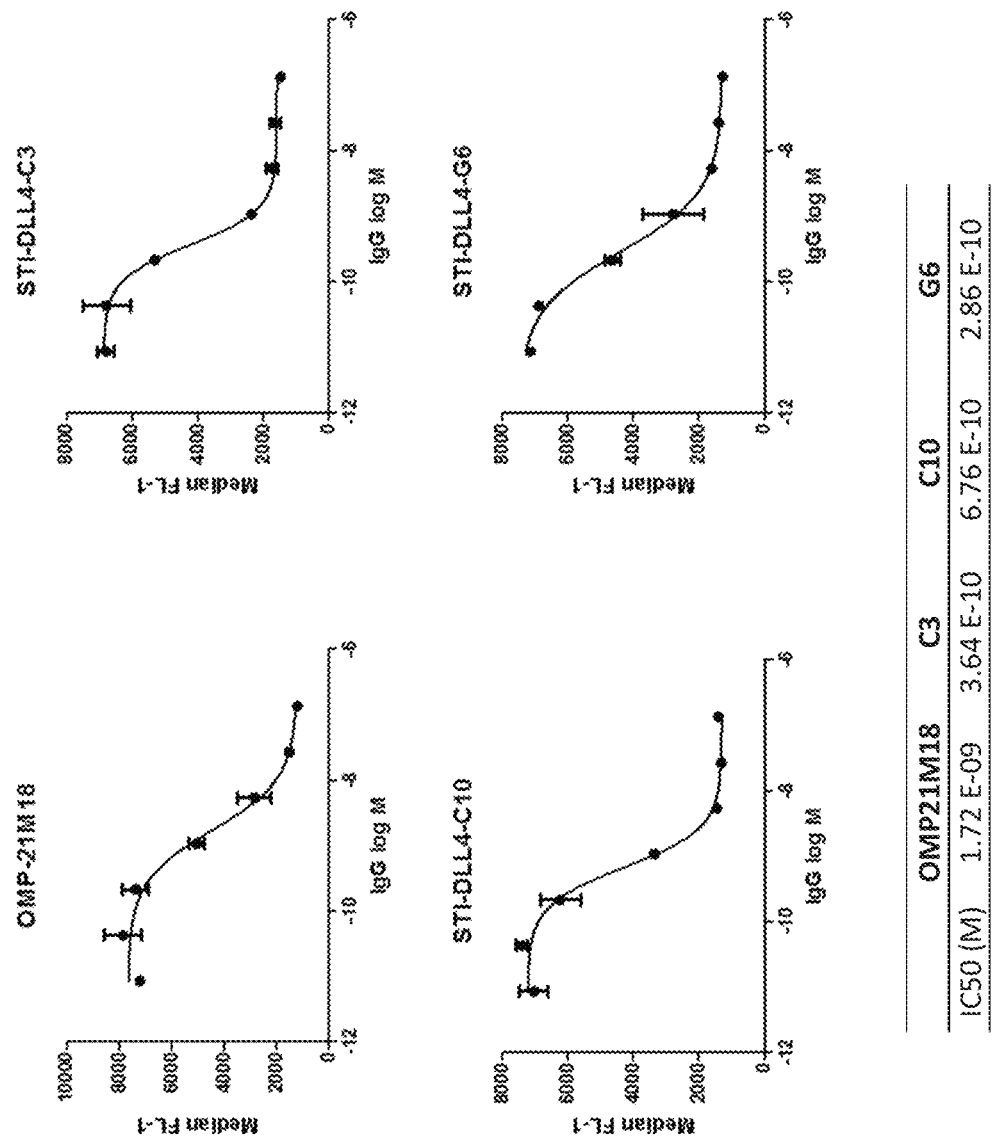

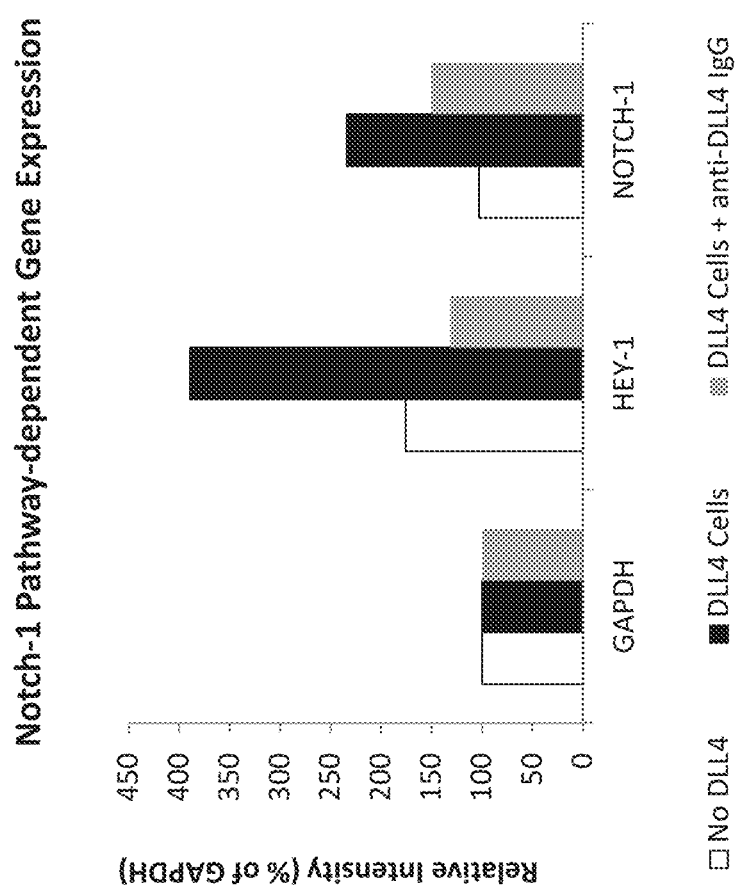
Fig 5. Anti-DLL4 antibodies inhibit DLL4-mediated Notch-1 Pathway activation.

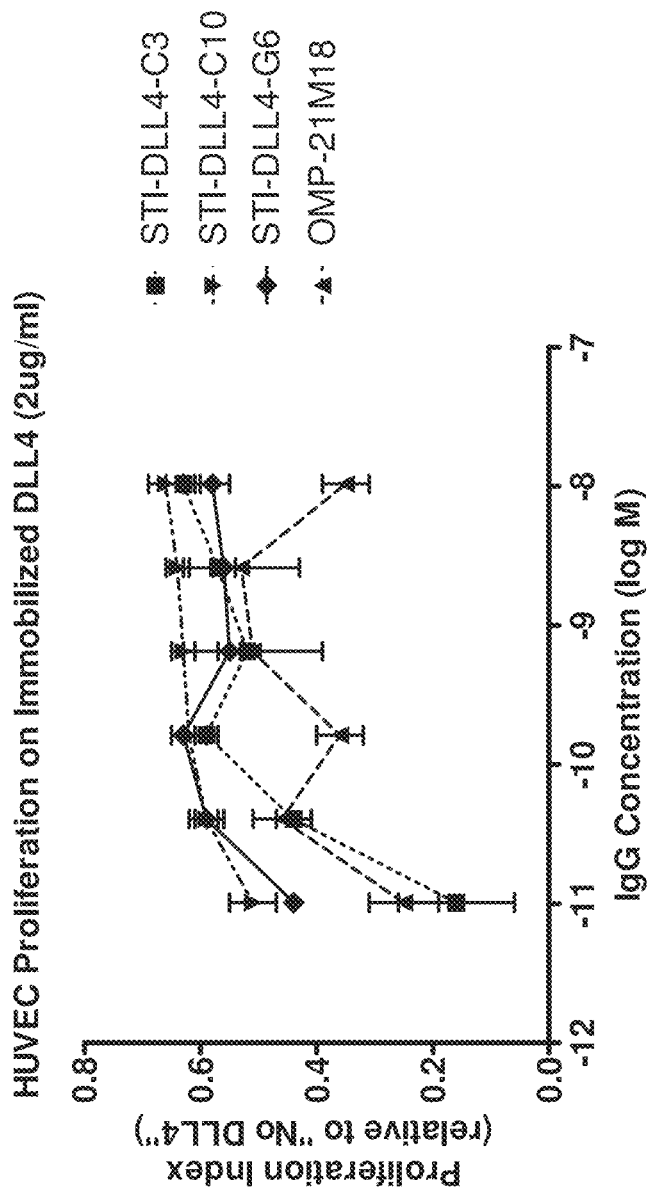
Fig 6. Anti-DLL4 antibodies block DLL4 mediated HUVEC Cell Growth Inhibition.

SEQUENCE LISTING

<160> NUMBER OF SEQ ID NOS: 40

<210> SEQ ID NO 1
<211> LENGTH: 122
<212> TYPE: PRT
<213> ORGANISM: Homo sapians

<400> SEQUENCE: 1

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Val Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Tyr Tyr Asp Ser Ser Gly Tyr Val Asp Phe Asp Tyr Trp
            100                 105                 110

Gly Gln Gly Thr Leu Val Thr Val Ser Ser
            115                 120

<210> SEQ ID NO 2
<211> LENGTH: 110
<212> TYPE: PRT
<213> ORGANISM: Homo sapians

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Pro
                85                  90                  95

Asn Gly Pro Val Phe Gly Gly Gly Thr Lys Leu Thr Val Leu
            100                 105                 110

<210> SEQ ID NO 3
<211> LENGTH: 121
<212> TYPE: PRT
<213> ORGANISM: Homo sapians

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Phe Glu
        35                  40                  45

```
Trp Leu Gly Arg Thr Glu Tyr Arg Ser Lys Trp Tyr Asn Asp Tyr Ala
     50                  55                  60

Val Ser Val Glu Ser Arg Ile Thr Ile Asn Pro Asp Thr Ser Lys Asn
 65                  70                  75                  80

His Phe Ser Leu Gln Leu Asn Ser Val Thr Pro Glu Asp Thr Ala Val
                 85                  90                  95

Tyr Tyr Cys Ala Arg Asp Gly Asn Thr Phe Ser Phe Asp Tyr Trp Gly
                100                 105                 110

Gln Gly Thr Leu Val Thr Val Ser Ser
                115                 120

<210> SEQ ID NO 4
<211> LENGTH: 110
<212> TYPE: PRT
<213> ORGANISM: Homo sapians

<400> SEQUENCE: 4

Gln Ser Val Val Thr Gln Pro Pro Ser Val Ser Ala Ala Pro Gly Gln
  1               5                  10                  15

Lys Val Thr Ile Ser Cys Ser Gly Gly Ser Ser Asn Ile Gly Asn Asn
                 20                  25                  30

Tyr Val Ser Trp Tyr Gln Gln Ile Pro Gly Thr Ala Pro Lys Leu Leu
                 35                  40                  45

Ile Tyr Asp Asn Asn Asn Arg Pro Ser Gly Ile Pro Asp Arg Phe Ser
     50                  55                  60

Gly Ser Lys Ser Gly Ala Ser Ala Thr Leu Gly Ile Ser Gly Leu Gln
 65                  70                  75                  80

Thr Gly Asp Glu Ala Asn Tyr Tyr Cys Gly Ala Trp Asp Ser Thr Leu
                 85                  90                  95

Ser Gly Tyr Val Phe Gly Thr Gly Thr Lys Leu Thr Val Leu
                100                 105                 110

<210> SEQ ID NO 5
<211> LENGTH: 117
<212> TYPE: PRT
<213> ORGANISM: Homo sapians

<400> SEQUENCE: 5

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gln Gly Leu Glu Trp Met Gly
                 35                  40                  45

Ile Ile Asn Pro Ser Gly Gly Ser Thr Ser Tyr Ala Gln Lys Phe Gln
     50                  55                  60

Gly Arg Val Thr Met Thr Arg Asp Thr Ser Thr Asn Thr Val Tyr Met
 65                  70                  75                  80

Glu Leu Ser Ser Leu Arg Ser Glu Asp Thr Ala Val Tyr Tyr Cys Ala
                 85                  90                  95

Arg Asp Val Trp Gly Gly Tyr Phe Asp Tyr Trp Gly Gln Gly Thr Leu
                100                 105                 110

Val Thr Val Ser Ser
        115

<210> SEQ ID NO 6
```

```
<211> LENGTH: 110
<212> TYPE: PRT
<213> ORGANISM: Homo sapians

<400> SEQUENCE: 6

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Ile Phe Gly Gly Gly Thr Lys Leu Thr Val Leu
            100                 105                 110

<210> SEQ ID NO 7
<211> LENGTH: 118
<212> TYPE: PRT
<213> ORGANISM: Homo sapians

<400> SEQUENCE: 7

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Ser Asn Gly
            20                  25                  30

Trp Met Thr Trp Leu Arg Gln Ala Pro Gly Lys Gly Leu Glu Trp Val
        35                  40                  45

Ala Thr Ile Lys Pro Asp Gly Ser Asp Thr Ala Tyr Val Glu Ser Val
50                  55                  60

Lys Gly Arg Phe Thr Ile Ser Arg Asp Asn Ala Lys Asn Leu Leu Tyr
65                  70                  75                  80

Leu Gln Met Asp Ser Leu Arg Gly Asp Asp Thr Ala Val Tyr Phe Cys
                85                  90                  95

Ala Arg Asp Leu Ala Tyr Asn Ala Phe Asp Ile Trp Gly Gln Gly Thr
            100                 105                 110

Met Val Thr Val Ser Ser
        115

<210> SEQ ID NO 8
<211> LENGTH: 110
<212> TYPE: PRT
<213> ORGANISM: Homo sapians

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60
```

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Tyr Val Phe Gly Thr Gly Thr Lys Leu Thr Val Leu
            100                 105                 110

<210> SEQ ID NO 9
<211> LENGTH: 124
<212> TYPE: PRT
<213> ORGANISM: Homo sapians

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Ser Pro Ser Gly Asp Ser Thr Tyr Ala Gln Lys Phe
        50                  55                  60

Gln Gly Arg Val Thr Met Thr Lys Asp Thr Ser Thr Ser Thr Val Ser
65                  70                  75                  80

Met Glu Leu Ser Ser Leu Arg Ser Glu Asp Thr Ala Val Tyr Tyr Cys
                85                  90                  95

Ala Arg Asp Gln Glu Gly Leu Arg Gly Ser Tyr Tyr Gly Met Asp
            100                 105                 110

Val Trp Gly Gln Gly Thr Thr Val Thr Val Ser Ser
        115                 120

<210> SEQ ID NO 10
<211> LENGTH: 110
<212> TYPE: PRT
<213> ORGANISM: Homo sapians

<400> SEQUENCE: 10

Ser Gln Pro Val Leu Thr Gln Pro Ala Ser Val Ser Gly Ser Pro Gly
1               5                   10                  15

Gln Ser Ile Thr Ile Ser Cys Thr Gly Thr Ser Ser Asp Ile Gly Asp
                20                  25                  30

Tyr Asn Tyr Val Ser Trp Tyr Gln Gln His Pro Gly Lys Ala Pro Lys
            35                  40                  45

Leu Met Ile Tyr Glu Val Ser Lys Arg Pro Ser Gly Val Pro Asp Arg
        50                  55                  60

Phe Ser Gly Ser Lys Ser Gly Asn Thr Ala Ser Leu Thr Ile Ser Gly
65                  70                  75                  80

Leu Gln Ala Glu Asp Glu Ala Asp Tyr Tyr Cys Tyr Ser Tyr Ala Gly
                85                  90                  95

Ser Tyr Thr Tyr Val Phe Gly Thr Gly Thr Lys Leu Thr Val
            100                 105                 110

<210> SEQ ID NO 11
<211> LENGTH: 119
<212> TYPE: PRT
<213> ORGANISM: Homo sapians

<400> SEQUENCE: 11

Gln Val Gln Leu Val Glu Ser Gly Ala Glu Val Lys Lys Pro Gly Ala

```
           1               5                  10                 15
          Ser Val Lys Val Ser Cys Lys Ala Ser Gly Tyr Thr Phe Thr Thr Tyr
                          20                  25                 30

Phe Ile His Trp Val Arg Gln Ala Pro Gly Gln Gly Leu Glu Trp Met
                          35                  40                 45

Gly Ile Ile Asn Pro Ser Gly Gly Ser Thr Ser Tyr Ala Gln Lys Phe
                          50                  55                 60

Gln Gly Arg Val Thr Met Thr Arg Asp Thr Ser Thr Ser Thr Val Tyr
          65                              70                  75              80

Met Glu Leu Ser Ser Leu Arg Ser Glu Asp Thr Ala Val Tyr Tyr Cys
                          85                  90                 95

Ala Arg Glu Phe Met Ala Thr Gly Gly Phe Asp Tyr Trp Gly Gln Gly
                          100                 105                110

Thr Leu Val Thr Val Ser Ser
                          115

<210> SEQ ID NO 12
<211> LENGTH: 111
<212> TYPE: PRT
<213> ORGANISM: Homo sapians

<400> SEQUENCE: 12

Gln Pro Val Leu Thr Gln Pro Ala Ser Val Ser Gly Ser Pro Gly Gln
          1               5                  10                 15

Ser Ile Thr Ile Pro Cys Thr Gly Thr Arg Ser Asp Val Gly Gly Tyr
                          20                  25                 30

Asn Phe Val Ser Trp Tyr Gln Gln His Pro Gly Lys Ala Pro Lys Leu
                          35                  40                 45

Leu Ile Tyr Asp Asn Asn Lys Arg Pro Ser Gly Ile Pro Gly Arg Phe
                          50                  55                 60

Ser Gly Ser Lys Ser Gly Thr Ser Ala Thr Leu Gly Ile Thr Gly Leu
          65                              70                  75              80

Gln Thr Gly Asp Glu Ala Asp Tyr Tyr Cys Gly Thr Trp Asp Asp Ser
                          85                  90                 95

Leu Asn Val Trp Val Phe Gly Gly Gly Thr Lys Val Thr Val Leu
                          100                 105                110

<210> SEQ ID NO 13
<211> LENGTH: 124
<212> TYPE: PRT
<213> ORGANISM: Homo sapians

<400> SEQUENCE: 13

Glu Val Gln Leu Val Gln Ser Gly Ala Glu Val Lys Lys Pro Gly Ala
          1               5                  10                 15

Ser Val Lys Val Ser Cys Lys Ala Ser Gly Tyr Ser Phe Met Asn Tyr
                          20                  25                 30

Asp Val Thr Trp Val Arg Gln Ala Ala Gln Gly Leu Glu Trp Met Gly
                          35                  40                 45

Trp Met Asn Pro Asp Ser Gly Asn Thr Gly Tyr Ala Asp Gln Phe Gln
                          50                  55                 60

Gly Arg Ile Thr Met Thr Arg Asp Thr Ser Lys Ser Thr Ala Tyr Met
          65                              70                  75              80

Glu Leu Thr Ser Leu Arg Ser Asp Asp Thr Ala Val Tyr Phe Cys Ala
                          85                  90                 95

Arg Ala Glu Val Glu Val Pro Gly Tyr Tyr Tyr Lys Tyr Gly Met Asp
```

```
                    100                 105                 110
Val Trp Gly Gln Gly Thr Thr Val Thr Val Ser Ser
            115                 120

<210> SEQ ID NO 14
<211> LENGTH: 108
<212> TYPE: PRT
<213> ORGANISM: Homo sapians

<400> SEQUENCE: 14

Ala Ile Arg Met Thr Gln Ser Pro Ser Phe Leu Ser Ala Ser Val Gly
1               5                   10                  15

Asp Arg Ile Thr Ile Thr Cys Arg Ala Ser Gln Asp Ile Ser Ala Tyr
            20                  25                  30

Leu Ala Trp Tyr Gln Gln Lys Pro Gly Thr Ala Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Tyr Asp Tyr Leu Pro
                85                  90                  95

Ile Thr Phe Gly Pro Gly Thr Lys Val Asp Ile Lys
            100                 105

<210> SEQ ID NO 15
<211> LENGTH: 119
<212> TYPE: PRT
<213> ORGANISM: Homo sapians

<400> SEQUENCE: 15

Gln Val Gln Leu Val Gln Ser Gly Ala Glu Val Lys Lys Pro Gly Glu
1               5                   10                  15

Ser Val Ile Ile Ser Cys Lys Ser Gly Phe Thr Phe Thr Arg Thr
            20                  25                  30

Ala Ile His Trp Met Arg Gln Ala Pro Gly Gln Ser Phe Glu Trp Val
        35                  40                  45

Gly Trp Ile Arg Gly Ser Asn Gly Asp Thr Ser Tyr Ser Gln Lys Phe
    50                  55                  60

Arg Asp Lys Val Thr Val Thr Ala Asp Thr Phe Ser Ser Thr Ser Tyr
65                  70                  75                  80

Leu Ala Leu Asn Arg Leu Thr Ser Glu Asp Thr Ala Val Tyr Tyr Cys
                85                  90                  95

Ala Arg Glu His Pro Thr Ser Trp Asp Pro Asp Phe Trp Gly Gln Gly
            100                 105                 110

Thr Leu Val Thr Val Ser Ser
        115

<210> SEQ ID NO 16
<211> LENGTH: 111
<212> TYPE: PRT
<213> ORGANISM: Homo sapians

<400> SEQUENCE: 16

Leu Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30
```

Asn Tyr Val Ser Trp Tyr Gln His His Pro Gly Lys Ala Pro Lys Leu
            35                  40                  45

Met Ile Tyr Asp Val Thr Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Pro Tyr Val Phe Gly Thr Gly Thr Lys Val Thr Val Leu
                100                 105                 110

<210> SEQ ID NO 17
<211> LENGTH: 123
<212> TYPE: PRT
<213> ORGANISM: Homo sapians

<400> SEQUENCE: 17

Gln Val Gln Leu Gln Gln Ser Gly Pro Gly Leu Val Gln Pro Ser Gln
 1               5                   10                  15

Thr Leu Ser Leu Thr Cys Val Ile Ser Gly Asp Ser Val Ser Asn Asn
                20                  25                  30

Asn Ala Ala Trp Thr Trp Ile Arg Gln Ser Pro Ser Arg Gly Leu Glu
            35                  40                  45

Trp Leu Gly Arg Thr Tyr Tyr Arg Ser Gln Trp Tyr Ser Asp Tyr Ala
 50                  55                  60

Val Ser Val Lys Ser Arg Met Thr Ile Asn Pro Asp Thr Ser Lys Asn
 65                  70                  75                  80

Gln Phe Ser Leu Gln Leu Asn Ser Leu Thr Pro Glu Asp Thr Ala Val
                85                  90                  95

Tyr Tyr Cys Ala Arg Glu Glu Val Met Asp His Asp Ala Phe Asp Ile
                100                 105                 110

Trp Gly Pro Gly Thr Met Val Thr Val Ser Ser
            115                 120

<210> SEQ ID NO 18
<211> LENGTH: 110
<212> TYPE: PRT
<213> ORGANISM: Homo sapians

<400> SEQUENCE: 18

Leu Pro Val Leu Thr Gln Ser Pro Ser Ala Ser Gly Thr Pro Gly Gln
 1               5                   10                  15

Arg Val Thr Ile Ser Cys Ser Gly Ser Thr Ser Asn Ile Gly Ser Asn
                20                  25                  30

Thr Val Asn Trp Tyr Gln Gln Phe Pro Gly Thr Ala Pro Lys Leu Leu
            35                  40                  45

Ile Tyr Tyr Asn Asp Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Arg Leu
                85                  90                  95

Tyr Gly Arg Leu Phe Gly Gly Gly Thr Lys Leu Ile Val Leu
                100                 105                 110

<210> SEQ ID NO 19

```
<211> LENGTH: 118
<212> TYPE: PRT
<213> ORGANISM: Homo sapians

<400> SEQUENCE: 19
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Phe | Asn | Val | Ser | Lys | Asn |
| | | | 20 | | | | | 25 | | | | | 30 | | |
| Tyr | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Ser | Met | Ser | Ser | Ser | Ser | Tyr | Lys | Tyr | Tyr | Ala | Asp | Ser | Val |
| | 50 | | | | | 55 | | | | | 60 | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Asn | Asp | Arg | Glu | Ala | Phe | Asp | Ile | Trp | Gly | Gln | Gly | Thr |
| | | | 100 | | | | | 105 | | | | | 110 | | |
| Met | Val | Thr | Val | Ser | Ser |
| | | | 115 | | |

```
<210> SEQ ID NO 20
<211> LENGTH: 107
<212> TYPE: PRT
<213> ORGANISM: Homo sapians

<400> SEQUENCE: 20
```

| | | | | | | | | | | | | | | | |
|---|---|---|---|---|---|---|---|---|---|---|---|---|---|---|---|
| Glu | Ile | Val | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Ser | Ile | Ser | Ser | Tyr |
| | | | 20 | | | | | 25 | | | | | 30 | | |
| Leu | Asn | Trp | Tyr | Gln | Gln | Lys | Pro | Gly | Lys | Ala | Pro | Lys | Leu | Leu | Ile |
| | | | 35 | | | | | 40 | | | | | 45 | | |
| Tyr | Ala | Ala | Ser | Ser | Leu | Gln | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Ser | Tyr | Ser | Thr | Pro | Leu |
| | | | | 85 | | | | | 90 | | | | | 95 | |
| Thr | Phe | Gly | Gln | Gly | Thr | Arg | Leu | Glu | Ile | Lys |
| | | | 100 | | | | | 105 | | |

```
<210> SEQ ID NO 21
<211> LENGTH: 120
<212> TYPE: PRT
<213> ORGANISM: Homo sapians

<400> SEQUENCE: 21
```

| | | | | | | | | | | | | | | | |
|---|---|---|---|---|---|---|---|---|---|---|---|---|---|---|---|
| Gln | Val | Gln | Leu | Gln | Gln | Ser | Gly | Pro | Gly | Leu | Val | Lys | Pro | Ser | Gln |
| 1 | | | | 5 | | | | | 10 | | | | | 15 | |
| Thr | Leu | Ser | Leu | Thr | Cys | Ala | Ile | Ser | Gly | Asp | Ser | Val | Ser | Ser | Asn |
| | | | 20 | | | | | 25 | | | | | 30 | | |
| Gly | Val | Ala | Trp | Asn | Trp | Ile | Arg | Gln | Ser | Pro | Ser | Arg | Gly | Leu | Glu |
| | | | 35 | | | | | 40 | | | | | 45 | | |
| Trp | Leu | Gly | Arg | Thr | Tyr | Phe | Asn | Ser | Lys | Trp | Tyr | Asn | Asp | Tyr | Ala |
| | 50 | | | | | 55 | | | | | 60 | | | | |

```
Val Ser Val Glu Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Arg Val Ser Ala Phe Asp Tyr Trp Gly Gln
            100                 105                 110

Gly Thr Pro Val Thr Val Ser Ser
            115                 120

<210> SEQ ID NO 22
<211> LENGTH: 110
<212> TYPE: PRT
<213> ORGANISM: Homo sapians

<400> SEQUENCE: 22

Gln Pro Val Leu Thr Gln Pro Ala Ser Val Ser Gly Ser Pro Gly Gln
  1               5                  10                  15

Ser Ile Thr Ile Ser Cys Thr Gly Thr Ser Asn Asp Val Gly Ser Tyr
                 20                  25                  30

Asp Leu Val Ser Trp Tyr Gln Gln His Pro Gly Lys Ala Pro Lys Leu
             35                  40                  45

Met Thr Tyr Asp Val Ser Asn Arg Pro Ser Gly Val Ser Asn Arg Phe
 50                  55                  60

Ser Gly Ala Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                 85                  90                  95

Ser Thr Val Val Phe Gly Gly Gly Thr Lys Leu Thr Val Leu
            100                 105                 110

<210> SEQ ID NO 23
<211> LENGTH: 125
<212> TYPE: PRT
<213> ORGANISM: Homo sapians

<400> SEQUENCE: 23

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Asp
                 20                  25                  30

Glu Ile Asn Trp Val Arg Gln Ala Thr Gly Gln Gly Leu Glu Trp Leu
             35                  40                  45

Gly Trp Met Asn Pro His Ser Gly Asn Thr Gly Tyr Ala Gln Lys Phe
 50                  55                  60

Gln Gly Arg Val Thr Met Thr Arg Asn Thr Ser Ile Ser Thr Ala Asp
 65                  70                  75                  80

Met Glu Leu Ser Ser Leu Thr Ser Asp Asp Thr Ala Val Tyr Tyr Cys
                 85                  90                  95

Ala Arg Gly His Tyr Tyr Glu Ser Ser Gly Tyr Phe Phe Tyr Gly Met
            100                 105                 110

Asp Val Trp Gly Gln Gly Thr Thr Val Thr Val Ser Ser
            115                 120                 125

<210> SEQ ID NO 24
<211> LENGTH: 110
<212> TYPE: PRT
<213> ORGANISM: Homo sapians
```

```
<400> SEQUENCE: 24

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Phe Gln Gln His Pro Gly Lys Ala Pro Lys Leu
            35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gly Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 25
<211> LENGTH: 123
<212> TYPE: PRT
<213> ORGANISM: Homo sapians

<400> SEQUENCE: 25

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Asp Asp Tyr Gly Asp His Phe Asp Tyr
            100                 105                 110

Trp Gly Gln Gly Thr Leu Val Thr Val Ser Ser
        115                 120

<210> SEQ ID NO 26
<211> LENGTH: 110
<212> TYPE: PRT
<213> ORGANISM: Homo sapians

<400> SEQUENCE: 26

Gln Ser Val Leu Thr Gln Pro Pro Ser Val Ser Glu Ala Pro Arg Gln
1               5                   10                  15

Gly Val Thr Ile Ser Cys Ser Gly Ser Arg Ser Asn Ile Gly Asn Asn
                20                  25                  30

Pro Val Ser Trp Tyr Gln Gln Val Pro Gly Lys Pro Pro Lys Leu Leu
            35                  40                  45

Ile Tyr Phe Asp Asp Leu Leu Pro Ser Gly Val Ser Asp Arg Phe Ser
        50                  55                  60

Ala Ser Lys Ser Gly Thr Ser Ala Ser Leu Ala Ile Ser Gly Leu Gln
65                  70                  75                  80

Ser Asp Asp Glu Ala Asp Tyr Phe Cys Ala Ala Trp Asp Ser Leu
```

```
                    85                  90                  95

Asn Gly Arg Val Phe Gly Gly Gly Thr Lys Leu Thr Val Leu
                100                 105                 110

<210> SEQ ID NO 27
<211> LENGTH: 119
<212> TYPE: PRT
<213> ORGANISM: Homo sapians

<400> SEQUENCE: 27

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Leu
            35                  40                  45

Gly His Ile Asn Ala Ala Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Arg Ser Gly Ser Tyr Leu Val Asp Tyr Trp Gly Gln Gly
                100                 105                 110

Thr Leu Val Thr Val Ser Ser
            115

<210> SEQ ID NO 28
<211> LENGTH: 109
<212> TYPE: PRT
<213> ORGANISM: Homo sapians

<400> SEQUENCE: 28

Tyr Val Leu Thr Gln Pro Pro Ser Ala Ser Gly Thr Pro Gly Gln Arg
1               5                   10                  15

Val Thr Ile Ser Cys Ser Gly Ser Asn Ser Asn Ile Gly Ser Asn Ala
                20                  25                  30

Val Asn Trp Tyr Gln His Leu Pro Gly Thr Ala Pro Lys Leu Leu Ile
            35                  40                  45

Tyr Ser Asn Asn Gln Arg Pro Ser Gly Val Pro Asp Arg Phe Ser Gly
        50                  55                  60

Ser Lys Ser Gly Thr Ser Ala Ser Leu Ala Ile Ser Gly Leu Gln Ser
65                  70                  75                  80

Glu Asp Glu Ser Asp Tyr Tyr Cys Ile Ala Trp Asp Gly Ser Leu Ser
                85                  90                  95

Gly Tyr Val Phe Gly Thr Gly Thr Lys Val Thr Val Leu
                100                 105

<210> SEQ ID NO 29
<211> LENGTH: 120
<212> TYPE: PRT
<213> ORGANISM: Homo sapians

<400> SEQUENCE: 29

Gln Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Asp Tyr
                20                  25                  30
```

```
Ala Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Ala Ala Val Tyr Tyr Cys
                85                  90                  95

Ala Arg Gly Asn Gly Ser Gly Ser Tyr Leu Val Asp Tyr Trp Gly Gln
                100                 105                 110

Gly Thr Leu Val Thr Val Ser Ser
            115                 120

<210> SEQ ID NO 30
<211> LENGTH: 110
<212> TYPE: PRT
<213> ORGANISM: Homo sapians

<400> SEQUENCE: 30

Gln Ser Val Val Thr Gln Pro Pro Ser Leu Ser Ala Ala Pro Gly Gln
1               5                   10                  15

Arg Val Ser Ile Ser Cys Ser Gly Thr Ser Ser Asn Ile Gly Lys Asn
                20                  25                  30

Tyr Val Ser Trp Tyr Gln Gln Val Pro Gly Thr Ala Pro Arg Leu Leu
            35                  40                  45

Ile Tyr Asp Asn Asn Lys Arg Ala Ser Gly Ile Pro Ala Arg Phe Ser
        50                  55                  60

Gly Ser Lys Ser Ala Thr Ser Ala Thr Leu Asp Ile Ala Gly Leu Gln
65                  70                  75                  80

Thr Gly Asp Glu Ala Asp Tyr Phe Cys Glu Thr Trp Asp Ser Ser Leu
                85                  90                  95

Arg Ala Glu Ile Phe Gly Gly Gly Thr Lys Leu Thr Val Leu
                100                 105                 110

<210> SEQ ID NO 31
<211> LENGTH: 121
<212> TYPE: PRT
<213> ORGANISM: Homo sapians

<400> SEQUENCE: 31

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Pro Met His Trp Val Arg Gln Ala Pro Gly Gln Arg Leu Glu Trp Met
            35                  40                  45

Gly Trp Ile Asn Ala Gly Asn Gly Asp Thr Lys Tyr Ser Gln Lys Phe
        50                  55                  60

Gln Asp Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Tyr Tyr Thr Ser Gly Thr Tyr Gln Ile Asp Tyr Trp Gly
                100                 105                 110

Gln Gly Thr Leu Val Thr Val Ser Ser
            115                 120
```

<210> SEQ ID NO 32
<211> LENGTH: 110
<212> TYPE: PRT
<213> ORGANISM: Homo sapians

<400> SEQUENCE: 32

Ser Tyr Glu Leu Met Gln Pro His Ser Val Ser Glu Ser Pro Gly Lys
1               5                   10                  15

Thr Val Thr Ile Ser Cys Thr Arg Ser Ser Gly Asn Ile Ala Ser Asn
            20                  25                  30

Tyr Val Arg Trp Tyr Gln Gln Arg Arg Asp Ser Ala Pro Thr Val Val
        35                  40                  45

Ile Phe Asp Asp Asp Gln Lys Pro Ser Gly Val Ala Asp Arg Phe Ser
    50                  55                  60

Gly Ser Ile Asp Thr Ser Ser Asn Ser Ala Ser Leu Thr Ile Ser Gly
65                  70                  75                  80

Leu Asn Thr Asp Asp Glu Ala Ala Tyr Tyr Cys His Ser Asp Glu Ser
                85                  90                  95

Ser Thr Val Ile Phe Gly Gly Arg Thr Lys Leu Thr Val Leu
            100                 105                 110

<210> SEQ ID NO 33
<211> LENGTH: 121
<212> TYPE: PRT
<213> ORGANISM: Homo sapians

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Phe Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Asn Ser Gly Gly Ser Leu Val Asp Tyr Trp Gly
            100                 105                 110

Gln Gly Thr Leu Val Thr Val Ser Ser
        115                 120

<210> SEQ ID NO 34
<211> LENGTH: 110
<212> TYPE: PRT
<213> ORGANISM: Homo sapians

<400> SEQUENCE: 34

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

```
Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Glu Val Phe Gly Thr Gly Thr Lys Val Thr Val Leu
            100                 105                 110

<210> SEQ ID NO 35
<211> LENGTH: 120
<212> TYPE: PRT
<213> ORGANISM: Homo sapians

<400> SEQUENCE: 35

Gln Val Gln Leu Val Gln Ser Gly Ala Glu Val Lys Lys Pro Gly Thr
1               5                   10                  15

Ser Val Lys Val Ser Cys Lys Thr Ser Gly Phe Pro Phe Thr Thr Tyr
                20                  25                  30

Phe Phe His Trp Ala Arg Gln Ala Pro Gly Gln Arg Pro Glu Trp Met
            35                  40                  45

Gly Trp Ile His Gly Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Ala Ala Val Tyr Tyr Cys
                85                  90                  95

Ala Arg Gly Asn Gly Ser Gly Ser Tyr Leu Val Asp Tyr Trp Gly Gln
            100                 105                 110

Gly Thr Leu Val Thr Val Ser Ser
        115                 120

<210> SEQ ID NO 36
<211> LENGTH: 110
<212> TYPE: PRT
<213> ORGANISM: Homo sapians

<400> SEQUENCE: 36

Gln Ala Gly Leu Thr Gln Pro Pro Ser Ala Ser Gly Ser Pro Gly Gln
1               5                   10                  15

Pro Val Thr Ile Ser Cys Ser Gly Thr Ser Gly Asp Val Gly Gly Tyr
                20                  25                  30

Asp Tyr Val Ser Trp Tyr Gln Gln His Pro Gly Lys Ala Pro Lys Leu
            35                  40                  45

Ile Ile Tyr Asp Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr His Cys Ser Ser Tyr Ala Gly Ser
                85                  90                  95

Asn Asn Val Ile Phe Gly Gly Gly Thr Lys Leu Thr Val Leu
            100                 105                 110

<210> SEQ ID NO 37
<211> LENGTH: 122
<212> TYPE: PRT
<213> ORGANISM: Homo sapians
```

<400> SEQUENCE: 37

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Phe Met His Trp Val Arg Gln Ala Pro Gly Gln Gly Leu Glu Trp Met
        35                  40                  45

Gly Val Ile Asn Pro Ser Gly Pro Gly Thr Thr Tyr Pro Gln Lys Phe
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp Leu Ile Asn Ser Gly Trp Ser Gly Ala Phe Asp Ile Trp
            100                 105                 110

Gly Gln Gly Thr Met Val Thr Val Ser Ser
            115                 120

<210> SEQ ID NO 38
<211> LENGTH: 108
<212> TYPE: PRT
<213> ORGANISM: Homo sapians

<400> SEQUENCE: 38

Gln Pro Val Leu Thr Gln Pro Pro Ser Val Ser Val Ala Pro Gly Asn
1               5                   10                  15

Thr Ala Ser Ile Thr Cys Gly Glu Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Ser
                85                  90                  95

Trp Val Phe Gly Gly Gly Thr Lys Val Thr Val Leu
            100                 105

<210> SEQ ID NO 39
<211> LENGTH: 119
<212> TYPE: PRT
<213> ORGANISM: Homo sapians

<400> SEQUENCE: 39

Gln Val Gln Leu Val Gln Ser Gly Ala Glu Val Lys Glu Pro Gly Ala
1               5                   10                  15

Ser Val Lys Val Ser Cys Lys Thr Ser Gly Phe Thr Phe Thr Gln Ile
            20                  25                  30

Tyr Val His Trp Val Arg Gln Ala Pro Gly Gln Gly Leu Glu Trp Met
        35                  40                  45

Gly Leu Val Arg Pro Ser Gly Ser Ser Arg Ile Tyr Gly Gln Asn Phe
    50                  55                  60

Gln Gly Arg Val Thr Leu Thr Arg Asp Thr Ser Thr Ser Thr Val Tyr
65                  70                  75                  80

Met Asp Leu Ser Ser Leu Thr Ser Glu Asp Thr Ala Val Tyr Tyr Cys

-continued

```
                85                  90                  95
Val Thr Asp Val Ala Gly Tyr Gly Asp Gly Arg Val Trp Gly Gln Gly
                100                 105                 110

Thr Leu Val Thr Val Ser Ser
        115

<210> SEQ ID NO 40
<211> LENGTH: 110
<212> TYPE: PRT
<213> ORGANISM: Homo sapians

<400> SEQUENCE: 40

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Ala Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Lys Leu Thr Val Leu
                100                 105                 110
```

METHODS FOR BLOCKING AN INTERACTION BETWEEN NOTCH-1 AND DELTA-LIKE 4 (DLL-4) BY ADMINISTERING A DDL-4 ANTIBODY

CROSS-REFERENCE TO RELATED APPLICATION

This patent application is a divisional of U.S. Ser. No. 13/903,793, filed May 28, 2013, which claims priority to U.S. provisional patent application 61/654,019 filed 31 May 2012.

TECHNICAL FIELD

The present disclosure provides compositions and methods relating to or derived from anti-DLL-4 antibodies. More specifically, the present disclosure provides human antibodies that bind DLL-4, DLL-4-binding fragments and derivatives of such antibodies, and DLL-4-binding polypeptides comprising such fragments. Further still, the present disclosure provides antibodies, antibody fragments and derivatives and polypeptides, and methods of using such antibodies, antibody fragments and derivatives and polypeptides, including methods of treating or diagnosing subjects having DLL-4-related disorders or conditions.

BACKGROUND

Cell-to-cell communication is required for many biological processes such as differentiation, proliferation, and homeostasis. One system utilized by a wide range of eukaryotes is the Notch-signaling pathway. This pathway, especially the Notch receptor, is also critical for functional tumor angiogenesis. Thus, inhibition of Notch receptor function, blockage of the Notch receptor, and/or blockage of the Notch-signaling pathway are potential strategies for anti-cancer compositions and therapies. Small molecule inhibitors of the Notch receptor have proven to be toxic because they suppress wild type (normal) tissue expression of Notch receptors throughout the body. Thus, different members of the Notch-signaling pathway should be considered as potential targets fortherapeutics.

A vasculature ligand for the Notch receptor is Delta 4 or Delta-like 4 (DLL-4). Largely expressed in the vasculature, DLL-4 is critical for vascular development (Yan et al., *Clin. Cancer Res.*, 13(24): 7243-7246 (2007); Shutter et al., *Genes Dev.*, 14(11): 1313-1318 (2000); Gale et al., *Proc. Natl. Acad. Sci. USA*. 101(45): 15949-15954 (2004); Krebs et al., *Genes Dev.*, 14(11): 1343-1352 (2000)). Mice heterozygous for DLL-4 are embryonically lethal due to major defects in vascular development (Gale et al., *Proc. Natl. Acad. Sci. USA*, 101(45): 15949-15954 (2004); Duarte et al., *Genes Dev.*, 18(20): 2474-2478 (2004); Krebs et al., *Genes Dev.*, 18(20): 2469-2473 (2004)). The expression of DLL-4 can be induced by VEGF (Liu et al., *Mal. Cell. Biol.*, 23(1): 14-25 (2003); Lobov et al., *Proc. Natl. Acad. Sci. USA*, 104(9): 3219-3224 (2007)). In sum, DLL-4 can negatively regulate VEGF signaling, in part through repressing VEGFR2 and inducing VEGFR1 (Harrington et al., *Microvasc. Res.*, 75(2): 144-154 (2008); Suchting et al., *Proc. Natl. Acad. Sci. USA*, 104(9): 3225-3230 (2007)). Exquisite coordination between DLL4 and VEGF is essential for functional angiogenesis.

In addition to its physiological role. DLL-4 is up-regulated in tumor blood vessels (Gale et al., *Proc. Natl. Acad. Sci. USA*, 101(45): 15949-15954 (2004); Mailhos et al., *Differentiation*, 69(2-3): 135-144 (2001); Patel et al., *Cancer Res.*, 65(19): 8690-8697 (2005); Patel et al., *Clin. Cancer Res.*, 12(16): 4836-4844 (2006); Noguera-Troise et al., *Nature*, 444(7122): 1032-1037 (2006)). Blockade of DLL-4 potently inhibited primary tumor growth in multiple models (Noguera-Troise et al., *Nature*, 444(7122): 1032-1037 (2006); Ridgway et al., *Nature*, 444(7122): 1083-1087 (2006); Scehnet et al., *Blood*, 109(11): 4753-4760 (2007)). The inhibition of DLL-4 was even effective against tumors that are resistant to anti-VEGF therapy. The combinatorial inhibition of both DLL-4 and VEGF provided an enhanced anti-tumor activity. Interestingly, unlike VEGF inhibition that reduces tumor vessel formation, DLL-4 blockade leads to an increase in tumor vasculature density wherein the vessels are abnormal, cannot support efficient blood transport, and are effectively nonfunctional. Thus, DLL4 provides a potential target for cancer treatment.

Interactions between Notch receptors and their ligands represent an evolutionarily conserved pathway important not only for cell fate decisions but also in regulating lineage decisions in hematopoiesis and in the developing thymus (Artavanis-Tsakonas et al. 1999, *Science* 284:770-776; Skokos et al. 2007; *J. Exp. Med.* 204:1525-1531; and Amsen et al. 2004, *Cell* 117:515-526). It has been recently shown that DLL-4-Notch 1 inhibition leads to a complete block in T cell development accompanied by ectopic appearance of B cells and an expansion of dendritic cells (DC) that can arise from Pro-T cell to DC fate conversion within the thymus (Hozumi et al. 2008, *J. Exp. Med.* 205(11):2507-2513; Koch et al. 2008, *J. Exp. Med.* 205(11):2515-2523; and Feyerabend et al. 2009. *Immunity* 30:1-13). Thus, there is accumulating evidence that Notch signaling is critical for the determination of cell fate decision from hematopoietic progenitor cells. Furthermore, a feedback control of regulatory T cell (Treg) homeostasis by DCs in vivo has been shown (Darrasse-Jeze et al. 2009, *J. Exp. Med.* 206(9): 1853-1862). However, the role of Notch signaling in controlling the origin and the development of DCs and consequently Treg homeostasis is still unknown. This is a question that is clinically important because identifying new methods of inducing Treg expansion could be used as a treatment for autoimmunity diseases and disorders.

Other DLL antagonists and their uses are disclosed in WO 2007/143689, WO 2007/070671, WO 2008/076379, WO 2008/042236, and WO/2008/019144. Therefore, there is a need in the art for therapeutic agents capable of targeting the DLL-4-Notch pathway and thereby inhibiting, or even preventing, tumor angiogenesis and growth.

SUMMARY

The present disclosure provides a fully human antibody of an IgG class that binds to a DLL-4 epitope with a binding affinity of at least $10^{-6}$ M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called C3 herein), SEQ ID NO. 3/SEQ ID NO. 4 (called C5 herein), SEQ ID NO. 5/SEQ ID NO. 6 (called C10 herein), SEQ ID NO. 7/SEQ ID NO. 8 (called G6 herein), SEQ ID NO. 9/SEQ ID NO. 10 (called F11 herein), SEQ ID NO. 11/SEQ ID NO. 12 (called D2 herein), SEQ ID NO. 13/SEQ ID NO. 14 (called E10 herein), SEQ ID NO. 15/SEQ ID NO. 16 (called F12 herein), SEQ ID NO. 17/SEQ ID NO. 18 (called E5 herein), SEQ ID NO. 19/SEQ ID NO. 20 (called H2 herein), SEQ ID NO. 21/SEQ ID NO. 22 (called A1 herein). SEQ ID NO. 23/SEQ ID NO. 24 (called A2 herein), SEQ ID NO. 25/SEQ ID NO. 26 (called A11 herein), SEQ ID NO. 27/SEQ ID NO. 28 (called C12 herein), SEQ ID NO. 29/SEQ ID NO. 30 (called D9 herein). SEQ ID NO. 31/SEQ ID NO. 32 (called E3 herein), SEQ ID NO. 33/SEQ ID NO. 34 (called E6 herein), SEQ ID NO. 35/SEQ ID NO. 36 (called F1 herein), SEQ ID NO. 37/SEQ ID NO. 38 (called F6 herein). SEQ ID NO. 39/SEQ ID NO. 40 (called F10 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2. SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6. SEQ ID NO. 7/SEQ ID NO. 8, SEQ ID NO. 9/SEQ ID NO. 10. SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18. SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21. SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8. SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22. SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32. SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

The present disclosure further provides a method for treating a broad spectrum of mammalian cancers, comprising administering an effective amount of an anti-DLL-4 polypeptide, wherein the anti-DLL-4 polypeptide is selected from the group consisting of a fully human antibody of an IgG class that binds to a DLL-4 epitope with a binding affinity of at least $10^{-6}$ M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5. SEQ ID NO. 7. SEQ ID NO. 9, SEQ ID NO. 11. SEQ ID NO. 13, SEQ ID NO. 15, SEQ ID NO. 17, SEQ ID NO. 19, SEQ ID NO. 21, SEQ ID NO. 23, SEQ ID NO. 25. SEQ ID NO. 27. SEQ ID NO. 29. SEQ ID NO. 31. SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2, SEQ ID NO. 4. SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof;

wherein the Fab fully human antibody fragment has the heavy chain variable domain sequence that is at least 95% identical to the amino acid sequences selected from the group consisting of SEQ ID NO. 1. SEQ ID NO. 3. SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23. SEQ ID NO. 25. SEQ ID NO. 27. SEQ ID NO. 29. SEQ ID NO. 31. SEQ ID NO. 33, SEQ ID NO. 35, SEQ ID NO. 37, SEQ ID NO. 39, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10. SEQ ID NO. 12. SEQ ID NO. 14. SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called C3 herein), SEQ ID NO. 3/SEQ ID NO. 4 (called C5 herein), SEQ ID NO. 5/SEQ ID NO. 6 (called C10 herein), SEQ ID NO. 7/SEQ ID NO. 8 (called G6 herein), SEQ ID NO. 9/SEQ ID NO. 10 (called F11 herein), SEQ ID NO. 11/SEQ ID NO. 12 (called D2 herein), SEQ ID NO. 13/SEQ ID NO. 14 (called E10 herein), SEQ ID NO. 15/SEQ ID NO. 16 (called F12 herein), SEQ ID NO. 17/SEQ ID NO. 18 (called E5 herein), SEQ ID NO. 19/SEQ ID NO. 20 (called H2 herein), SEQ ID NO. 21/SEQ ID NO. 22 (called A1 herein), SEQ ID NO. 23/SEQ ID NO. 24 (called A2 herein), SEQ ID NO. 25/SEQ ID NO. 26 (called A11 herein). SEQ ID NO. 27/SEQ ID NO. 28 (called C12 herein), SEQ ID NO. 29/SEQ ID NO. 30 (called D9 herein), SEQ ID NO. 31/SEQ ID NO. 32 (called E3 herein), SEQ ID NO. 33/SEQ ID NO. 34 (called E6 herein), SEQ ID NO. 35/SEQ ID NO. 36 (called F1 herein), SEQ ID NO. 37/SEQ ID NO. 38 (called F6 herein), SEQ ID NO. 39/SEQ ID NO. 40 (called F10 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called C3 herein), SEQ ID NO. 3/SEQ ID NO. 4 (called C5 herein), SEQ ID NO. 5/SEQ ID NO. 6 (called C10 herein), SEQ ID NO. 7/SEQ ID NO. 8 (called G6 herein), SEQ ID NO. 9/SEQ ID NO. 10 (called F11 herein), SEQ ID NO. 11/SEQ ID NO. 12 (called D2 herein), SEQ ID NO. 13/SEQ ID NO. 14 (called E10 herein), SEQ ID NO. 15/SEQ ID NO. 16 (called F12 herein), SEQ ID NO. 17/SEQ ID NO. 18 (called E5 herein), SEQ ID NO. 19/SEQ ID NO. 20 (called H2 herein), SEQ ID NO. 21/SEQ ID NO. 22 (called A1 herein), SEQ ID NO. 23/SEQ ID NO. 24 (called A2 herein), SEQ ID NO. 25/SEQ ID NO. 26 (called A11 herein), SEQ ID NO. 27/SEQ ID NO. 28 (called C12 herein), SEQ ID NO. 29/SEQ ID NO. 30 (called D9 herein), SEQ ID NO. 31/SEQ ID NO. 32 (called E3 herein), SEQ ID NO. 33/SEQ ID NO. 34 (called E6 herein), SEQ ID NO. 35/SEQ ID NO. 36 (called F1 herein), SEQ ID NO. 37/SEQ ID NO. 38 (called F6 herein), SEQ ID NO. 39/SEQ ID NO. 40 (called F10 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. S/SEQ ID NO. 6. SEQ ID NO. 7/SEQ ID NO. 8, SEQ ID NO. 9/SEQ ID NO. 10. SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18. SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

Preferably, the broad spectrum of mammalian cancers to be treated is selected from the group consisting of ovarian, colon, breast, lung cancers, myelomas, neuroblastic-derived CNS tumors, monocytic leukemias, B-cell derived leukemias. T-cell derived leukemias, B-cell derived lymphomas, T-cell derived lymphomas, mast cell derived tumors, and combinations thereof.

BRIEF DESCRIPTION OF THE FIGURES

FIG. 1A shows the initial screening binding of various anti-DLL-4 antibodies to cell surface expressed DLL-4. Cells stably expressing DLL-4 were incubated with 1 µg/ml of anti-DLL-4 antibodies as indicated. The binding was analyzed by flow cytometry (HTFC, Intellicyt).

FIG. 1B shows the binding of exemplary anti-DLL-4 antibodies to cell surface expressed DLL-4. Cells stably expressing DLL-4 were incubated with increasing amounts of anti-DLL-4 antibodies. The binding was analyzed by flow cytometry. Anti-DLL-4 antibodies showed binding characteristics ($EC_{50}$) comparable to or better than Oncomed OMP21M18.

FIG. 2 shows a Biacore analysis of various anti-DLL-4 antibodies. The resulting binding kinetic parameters are indicated in the accompanying table.

FIGS. 3A and 3B show epitope mapping of anti-DLL-4 antibodies in relation to Oncomed OMP21M18 antibody. Additional binding registered by Octet indicates that anti-DLL-4 antibodies C3, C5 or G6 binds to an epitope of DLL-4 that is not occupied by 21M18.

FIG. 4A shows how anti-DLL-4 antibodies block rhDLL4 binding to immobilized rrNotch. The greater the binding the higher the absorbance value, therefore the best blocking antibodies are C10 and G6 which show the lowest values and are comparable to Oncomed OMP21M18 on the basis of in vitro binding activity.

FIG. 4B shows that anti-DLL-4 antibodies block the binding of a soluble recombinant Notch-1 (either rat or human) to cellular human DLL-4, as measured by flow cytometry. In this assay, Notch-1 is fluorescently labeled, therefore a high Mean Fluorescence Intensity (MFI) would reflect a strong interaction between Notch-1 and DLL-4. In the presence of anti-DLL-4 antibodies, little to no fluorescence was detected indicating blocking of the interaction.

FIG. 4C shows the dose-dependent inhibition of the DLL-4-Notch-1 interaction for selected antibodies. $IC_{50}$ values reflect the concentration of antibody which causes 50% inhibition of interaction between soluble Notch-1 and DLL-4. Anti-DLL-4 antibodies disclosed within show greater inhibitory activity than OMP21M18.

FIG. 5 shows a RT-PCR-based bioassay that was developed to determine the ability of selected antibodies to neutralize DLL-4-mediated cellular function in vitro. Data show that anti-DLL-4 antibody C3, an exemplary antibody of this disclosure, was able to efficiently inhibit DLL-4-mediated activation of Notch-1 dependent gene expression in a breast cancer cell Line (MCF7).

FIG. 6 shows that anti-DLL-4 antibodies can prevent DLL-4-mediated HUVEC proliferation inhibition. DLL4 is known to inhibit VEGF-mediated HUVEC proliferation. Thus, when cultured on DLL-4-coated plate, HUVEC growth is inhibited. Data show that anti-DLL-4 antibodies were able to block this inhibition and to partially restore HUVEC growth.

DETAILED DESCRIPTION

The present disclosure provides a fully human antibody of an IgG class that binds to a DLL-4 epitope with a binding affinity of 10*M or less, that has a heavy chain variable domain sequence that is at least 95% identical to the amino acid sequences selected from the group consisting of SEQ ID NO. 1, SEQ ID NO. 3. SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23. SEQ ID NO. 25. SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called C3 herein), SEQ ID NO. 3/SEQ ID NO. 4 (called C5 herein), SEQ ID NO. 5/SEQ ID NO. 6 (called C10 herein), SEQ ID NO. 7/SEQ ID NO. 8 (called G6 herein). SEQ ID NO. 9/SEQ ID NO. 10 (called FI 1 herein), SEQ ID NO. 11/SEQ ID NO. 12 (called D2 herein), SEQ ID NO. 13/SEQ ID NO. 14 (called E10 herein), SEQ ID NO. 15/SEQ ID NO. 16 (called F12 herein), SEQ ID NO. 17/SEQ ID NO. 18 (called E5 herein), SEQ ID NO. 19/SEQ ID NO. 20 (called H2 herein), SEQ ID NO. 21/SEQ ID NO. 22 (called A1 herein). SEQ ID NO. 23/SEQ ID NO. 24 (called A2 herein), SEQ ID NO. 25/SEQ ID NO. 26 (called A11 herein), SEQ ID NO. 27/SEQ ID NO. 28 (called C12 herein), SEQ ID NO. 29/SEQ ID NO. 30 (called D9 herein). SEQ ID NO. 31/SEQ ID NO. 32 (called E3 herein), SEQ ID NO. 33/SEQ ID NO. 34 (called E6 herein), SEQ ID NO. 35/SEQ ID NO. 36 (called F1 herein), SEQ ID NO. 37/SEQ ID NO. 38 (called F6 herein), SEQ ID NO. 39/SEQ ID NO. 40 (called F10 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31. SEQ ID NO. 33. SEQ ID NO. 35. SEQ ID NO. 37. SEQ ID NO. 39, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2. SEQ ID NO. 3/SEQ ID NO. 4, SEQ ID NO. 5/SEQ ID NO. 6. SEQ ID NO. 7/SEQ ID NO. 8, SEQ ID NO. 9/SEQ ID NO. 10, SEQ ID NO. 11/SEQ ID NO. 12. SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2. SEQ ID NO. 4. SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24. SEQ ID NO. 26. SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4. SEQ ID NO. 5/SEQ ID NO. 6, SEQ ID NO. 7/SEQ ID NO. 8. SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28. SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

The present disclosure further provides a method for treating a broad spectrum of mammalian cancers, comprising administering an effective amount of an anti-DLL-4 polypeptide, wherein the anti-DLL-4 polypeptide is selected from the group consisting of a fully human antibody of an IgG class that binds to a DLL-4 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5. SEQ ID NO. 7. SEQ ID NO. 9, SEQ ID NO. 11. SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28. SEQ ID NO. 30. SEQ ID NO. 32, SEQ ID NO. 34, SEQ ID NO. 36, SEQ ID NO. 38, SEQ ID NO. 40, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3. SEQ ID NO. 5, SEQ ID NO. 7, SEQ ID NO. 9, SEQ ID NO. 11. SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32. SEQ ID NO. 34, SEQ ID NO. 36. SEQ ID NO. 38. SEQ ID NO. 40, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29. SEQ ID NO. 31. SEQ ID NO. 33. SEQ ID NO. 35, SEQ ID NO. 37, SEQ ID NO. 39, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10. SEQ ID NO. 12. SEQ ID NO. 14. SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4. SEQ ID NO. 5/SEQ ID NO. 6, SEQ ID NO. 7/SEQ ID NO. 8. SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16. SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28. SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12. SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24. SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38. SEQ ID NO. 39/SEQ ID NO. 40, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18. SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28. SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, and combinations thereof.

Preferably, the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example. Korndorfer et al., 2003, *Proteins: Structure. Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US App. Pub. 20/0202512; 2004/0202995; 2004/0038291; 2004/0009507; 2003/0039958, and Ward et al., *Nature* 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988. *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993. *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra: Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-DLL-4 antibody. In another embodiment, all of the CDRs are derived from a human anti-DLL-4 antibody. In another embodiment, the CDRs from more than one human anti-DLL-4 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-DLL-4 antibody, and the CDRs from the heavy chain from a third anti-DLL-4 antibody. Other combinations are possible.

Further, the framework regions may be derived from one of the same anti-DLL-4 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind DLL-4).

A "neutralizing antibody" or an "inhibitory antibody" is an antibody that inhibits the proteolytic activation of DLL-4 when an excess of the anti-DLL-4 antibody reduces the amount of activation by at least about 20% using an assay such as those described herein in the Examples. In various embodiments, the antigen binding protein reduces the amount of amount of proteolytic activation of DLL-4 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. (Bowie et al., 1991, *Science* 253:164).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human DLL-4) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego. Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-BI 1, which is deficient in DHFR (Urlaub et al., 1980, *Proc. Natl. Acad. Sci. USA* 77:4216-20), HeLa cells. BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression. Examples of nucleic acid sequences encoding VK-8B polypeptide disclosed herein are:

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. (Mayfield et al., *Proc. Natl. Acad. Sci. USA.* 2003 100(2):438-42; Sinclair et al. *Protein Expr. Purif.* 2002 (1):96-105; Connell, *Curr. Opin. Biotechnol.* 2001 12(5):446-9; Makrides et al. *Microbiol. Rev.* 1996 60(3):512-38; and Sharp et al. *Yeast.* 1991 7(7):657-78).

General techniques for nucleic acid manipulation are described for example in Sambrook et al., *Molecular Cloning: A Laboratory Manual*, Vols. 1-3, Cold Spring Harbor Laboratory Press, 2 ed., 1989, or Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. Moreover, a host can replicate, usually conferred by an origin of replication, and a selection gene to facilitate recognition of transformants.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

DLL-4-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. (Raju et al. *Biochemistry*. 2001 31; 40(30):8868-76). Effects of such non-amino acid elements on the functionality of a polypeptide may be tested for its antagonizing role in DLL-4 function, e.g., its inhibitory effect on angiogenesis or on tumor growth.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4.301.144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York. Vol. 3, pages 138-161). The term "PEG" is used broadly to encompass any polyethylene glycol molecule, without regard to size or to modification at an end of the PEG, and can be represented by the formula: X—O (CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

Although PEG is well-known, this is, to our knowledge, the first demonstration that a pegylated $^{10F}$n3 polypeptide can be pegylated and retain ligand binding activity. In a preferred embodiment, the pegylated $^{10F}$n3 polypeptide is produced by site-directed pegylation, particularly by conjugation of PEG to a cysteine moiety at the N- or C-terminus. Accordingly, the present disclosure provides a target-binding $^{10F}$n3 polypeptide with improved pharmacokinetic properties, the polypeptide comprising: a $^{10F}$n3 domain having from about 80 to about 150 amino acids, wherein at least one of the loops of said $^{10F}$n3 domain participate in target binding; and a covalently bound PEG moiety, wherein said $^{10F}$n3 polypeptide binds to the target with a $K_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{0F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.*, 252, 3571 (1977) and *J. Biol. Chem.*, 252, 3582 (1977). Zalipsky, et al., and Harris et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to DLL-4-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12.000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment a DLL-4 binding polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's 6-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group. One skilled in the art can select a suitable molecular mass for PEG, e.g., based on how the pegylated binding polypeptide will be used therapeutically, the desired dosage, circulation time, resistance to proteolysis, immunogenicity, and other considerations.

In one embodiment, PEG molecules may be activated to react with amino groups on a binding polypeptide, such as with lysines (Bencham et al., *Anal. Biochem.*, 131, 25 (1983); Veronese et al., *Appl. Biochem.*, 11, 141 (1985).; Zalipsky et al., *Polymeric Drugs and Drug Delivery Systems*, adrs 9-110 ACS Symposium Series 469 (1999); Zalipsky et al., *Europ. Polym. J.*, 19, 1177-1183 (1983); Delgado et al., *Biotechnology and Applied Biochemistry*, 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of a $^{10F}$n3 polypeptide can be performed according to the methods of the state of the art, for example by reaction of the binding polypeptide with electrophilically active PEGs (supplier. Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini et al., *Bioconjugate Chem.* 6 (1995) 62-69). Such methods may be used to pegylate at an f-amino group of a binding polypeptide lysine or the N-terminal amino group of the binding polypeptide.

In another embodiment, PEG molecules may be coupled to sulfhydryl groups on a binding polypeptide (Sartore et al., *Appl. Biochem. Biotechnol.*, 27, 45 (1991); Morpurgo et al., *Biocon. Chem.*, 7, 363-368 (1996); Goodson et al., *Bio/Technology* (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (Himanen et al., *Nature.* (2001) 20-27; 414(6866): 933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) *JPET,* 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) *J. Biol. Chem.* 254, 12579, and in Chamow et al., (1994) *Bioconjugate Chem.* 5, 133.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70%, 80%, 85%, 90%, 95% or 100% of the biological activity associated with the unmodified protein. In one embodiment, biological activity refers to its ability to bind to DLL-4, as assessed by KD, $k_{on}$, or $k_{off}$. In one specific embodiment, the pegylated binding polypeptide protein shows an increase in binding to DLL-4 relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Formulations and Modes of Administration

The present disclosure features methods for treating conditions or preventing pre-conditions which respond to an inhibition of DLL-4 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The DLL-4 binding proteins described herein and their related variants are useful in a number of therapeutic and diagnostic applications. These include the inhibition of the biological activity of DLL-4 by competing for or blocking the binding to a DLL-4 as well as the delivery of cytotoxic or imaging moieties to cells, preferably cells expressing DLL-4. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of DLL-4 biological activity, the polypeptides of this disclosure are effective against a number of cancer conditions as well as complications arising from cancer, such as pleural effusion and ascites. Preferably, the DLL-4-binding polypeptides of the disclosure can be used for the treatment of prevention of hyperproliferative diseases or cancer and the metastatic spread of cancers. Preferred indications for the disclosed anti-DLL-4 antibodies include colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

In addition, various inflammatory disorders can be treated with the disclosed anti-DLL-4 binding polypeptides disclosed herein. Such inflammatory disorders include, for example, intestinal mucosa inflammation wasting diseases associated with colitis, multiple sclerosis, rheumatoid arthritis, osteoarthritis, psoriasis, and Crohn's disease.

A DLL-4 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-DLL-4 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

The DLL-4 binding proteins described herein can also be detectably labeled and used to contact cells expressing DLL-4 for imaging applications or diagnostic applications. For diagnostic purposes, the polypeptide of the invention is preferably immobilized on a solid support. Preferred solid supports include columns (for example, affinity columns, such as agarose-based affinity columns), microchips, or beads.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of DLL-4. The levels of DLL-4 detected are then compared to levels of DLL-4 detected in a normal sample also contacted with the labeled polypeptide. An increase of at least 10%, 20%, 30%, 40%, 50%, 60%, 70%, 80%, or 90% in the levels of the DLL-4 may be considered a diagnostic indicator.

In certain embodiments, the DLL-4 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{124}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using DLL-4 binding polypeptides directed at DLL-4 may be used to detect and/or diagnose cancers and vasculature. For example, any of the binding polypeptide against a DLL-4 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The DLL-4 binding polypeptides can also be used to deliver additional therapeutic agents (including but not limited to drug compounds, chemotherapeutic compounds, and radiotherapeutic compounds) to a cell or tissue expressing DLL-4. In one example, the DLL-4 binding polypeptide is fused to a chemotherapeutic agent for targeted delivery of the chemotherapeutic agent to a tumor cell or tissue expressing DLL-4.

The DLL-4 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of DLL-4, for example, on endothelial cells (e.g., venous endothelial cells), or on cells transfected with a DLL-4 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to DLL-4. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a DLL-4 protein is combined with the subject binding polypeptides, binding occurs between the binding polypeptides and the DLL-4 protein. In one embodiment, a sample containing cells expressing a DLL-4 protein (e.g., endothelial cells) is combined with the subject antibodies, and binding occurs between the binding polypeptides and cells bearing a DLL-4 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a DLL-4 protein in a biological sample can also be prepared. Such kits will include a DLL-4 binding polypeptide which binds to a DLL-4 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of DLL-4, wherein a composition comprising a cell or fraction thereof (e.g., membrane fraction) is contacted with a binding polypeptide which binds to a DLL-4 or portion of the receptor under conditions appropriate for binding thereto, and the binding is monitored. Detection of the binding polypeptide, indicative of the formation of a complex between binding polypeptide and DLL-4 or a portion thereof, indicates the presence of the receptor. Binding of a polypeptide to the cell can be determined by standard methods, such as those described in the working examples. The method can be used to detect expression of DLL-4 on cells from an individual. Optionally, a quantitative expression of DLL-4 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of DLL-4 present on cells and/or the number of DLL-4-positive cells in a mammal. In one embodiment, the invention relates to a method of detecting susceptibility of a mammal to a tumor. In this embodiment, a sample to be tested is contacted with a binding polypeptide which binds to a DLL-4 or portion thereof under conditions appropriate for binding thereto, wherein the sample comprises cells which express DLL-4 in normal individuals. The binding and/or amount of binding is detected, which indicates the susceptibility of the individual to a tumor, wherein higher levels of receptor correlate with increased susceptibility of the individual to a tumor.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "DLL-4 inhibitor" and "DLL-4 antagonist" are used interchangeably. Each is a molecule that detectably inhibits at least one function of DLL-4. Conversely, a "DLL-4 agonist" is a molecule that detectably increases at least one function of DLL-4. The inhibition caused by a DLL-4 inhibitor need not be complete so long as it is detectable using an assay. Any assay of a function of DLL-4 can be used, examples of which are provided herein. Examples of functions of DLL-4 that can be inhibited by a DLL-4 inhibitor, or increased by a DLL-4 agonist, include cancer cell growth or apoptosis (programmed cell death), and so on. Examples of types of DLL-4 inhibitors and DLL-4 agonists include, but are not limited to, DLL-4 binding polypeptides such as antigen binding proteins (e.g., DLL-4 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example. Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG. IgA, and IgE, respectively. Preferably, the anti-DLL-4 antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human DLL-4) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175). L cells. C127 cells, 3T3 cells (ATCC CCL 163). Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to DLL-4, (preferably, human DLL-4). Antigen binding proteins include antigen binding proteins that inhibit a biological activity of DLL-4.

Oligomers that contain one or more antigen binding proteins may be employed as DLL-4 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have DLL-4 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990. *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a DLL-4 binding fragment of an anti-DLL-4 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-DLL-4 antibody fragment or derivative fused to a leucine zipper peptide are expressed in suitable host cells, and the soluble oligomeric anti-DLL-4 antibody fragments or derivatives that form are recovered from the culture supernatant.

The present disclosure provides a DLL-4 binding antigen binding protein (for example, an anti-DLL-4 antibody), that has one or more of the following characteristics: binds to both human and murine DLL-4, inhibits the activation of human DLL-4, inhibits the activation of murine DLL-4, binds to or near the proteolytic cleavage site of DLL-4, causes relatively little down-regulation of cell-surface expressed DLL-4.

Antigen-binding fragments of antigen binding proteins of the invention may be produced by conventional techniques. Examples of such fragments include, but are not limited to, Fab and $F(ab')_2$ fragments.

The present disclosure provides monoclonal antibodies that bind to DLL-4. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against DLL-4 can be used, for example, in assays to detect the presence of DLL-4 polypeptides, either in vitro or in vivo. The antigen binding proteins also may be employed in purifying DLL-4 proteins by immunoaffinity chromatography. Blocking antigen binding proteins can be used in the methods disclosed herein. Such antigen binding proteins that function as DLL-4 antagonists may be employed in treating any DLL-4-induced condition, including but not limited to various cancers.

Antigen binding proteins may be employed in an in vitro procedure, or administered in vivo to inhibit DLL-4-induced biological activity. Disorders caused or exacerbated (directly or indirectly) by the proteolytic activation of DLL-4, examples of which are provided herein, thus may be treated. In one embodiment, the present invention provides a therapeutic method comprising in vivo administration of a DLL-4 blocking antigen binding protein to a mammal in need thereof in an amount effective for reducing an DLL-4-induced biological activity.

Antigen binding proteins include fully human monoclonal antibodies that inhibit a biological activity of DLL-4.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses. Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells. HeLa cells. BHK (ATCC CRL 10) cell lines, and the CV1/EBNA cell line derived from the African green monkey kidney cell line CV1 (ATCC: CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of DLL-4 bound thereto. Polypeptides contemplated for use herein include substantially homogeneous recombinant mammalian anti-DLL-4 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-DLL-4 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for DLL-4 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from DLL-4. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to DLL-4 with substantially the same $K_{off}$ as an antibody described herein.

In another aspect, the present disclosure provides an antigen binding protein that inhibits an activity of DLL-4. In one embodiment, the antigen binding protein has an $IC_{50}$ of 1000 nM or lower. In another embodiment, the $IC_{50}$ is 100 nM or lower, in another embodiment, the $IC_{50}$ is 10 nM or lower. In another embodiment, the $IC_{50}$ is substantially the same as that of an antibody described herein in the Examples. In another embodiment, the antigen binding protein inhibits an activity of DLL-4 with substantially the same $IC_{50}$ as an antibody described herein.

In another aspect, the present disclosure provides an antigen binding protein that binds to human DLL-4 expressed on the surface of a cell and, when so bound, inhibits DLL-4 signaling activity in the cell without causing a significant reduction in the amount of DLL-4 on the surface of the cell. Any method for determining or estimating the amount of DLL-4 on the surface and/or in the interior of the cell can be used. In other embodiments, binding of the antigen binding protein to the DLL-4-expressing cell causes less than about 75%, 50%, 40%, 30%, 20%, 15%, 10%, 5%, 1%, or 0.1% of the cell-surface DLL-4 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of DLL-4, or to an epitope of DLL-4 and an epitope of another molecule, via two different antigen binding sites or regions. Moreover, bispecific antigen binding protein as disclosed herein can comprise a DLL-4 binding site from one of the herein-described antibodies and a second DLL-4 binding region from another of the herein-described antibodies, including those described herein by reference to other publications. Alternatively, a bispecific antigen binding protein may comprise an antigen binding site from one of the herein described antibodies and a second antigen binding site from another DLL-4 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds DLL-4 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an DLL-4 binding antigen binding protein.

Example 1

This example illustrates in vitro data for cell binding as part of an initial screen for several disclosed antibodies. CHO-K1 cells stably expressing DLL-4 (CHO-DLL-4 cells) were lifted in enzyme-free Dissociation Buffer and transferred to V-Bottom 96 well-plates (100,000 cells/well). Cells were incubated with anti-DLL-4 Antibodies in FACS buffer (PBS+2% FBS)+$NaN_3$ on ice for 45 min. After 2 washes in FACS buffer, a 1:1000 dilution of Phycoerythrin conjugated anti-Human IgG (γ-chain specific) was added and incubated for 30 min. Following a final wash, fluorescence intensity was measured on an Intellicyt High Throughput Flow Cytometer (HTFC). Data were analyzed using Graphpad Prism software using non-linear regression fit. Data points are shown as the median fluorescence intensity (MFI) of positively labeled cells +/− Standard Error. $EC_{50}$ values are reported as the concentration of antibody to achieve 50% of maximal DLL-4 antibodies binding to DLL-4 expressing cells.

Results: This example shows that the disclosed anti-DLL-4 monoclonal antibodies were able to bind efficiently to DLL-4 expressed on the surface of cells. Several disclosed antibodies showed more potent binding characteristics compared to anti-DLL-4 antibody OMP21M18 (Oncomed), currently in clinical trial. $EC_{50}$ values were calculated for the disclosed anti-DLL4 antibodies C3, C10 and G6, and range from 0.1 to 0.3 nM, compared to 1.7 nM for OMP21M18 (FIG. 2).

Example 2

This example illustrates an antigen binding affinity determination for disclosed anti-DLL4 antibodies C3, C6 and G6. Affinity Determination Using BIACORE® Surface Plasmon Resonance Technology. Recombinant hDLL4 was immobilized on CM5 sensor chip using standard NHS/EDC coupling methodology. All measurements were conducted in HBS-EP buffer with a flow rate of 30 μL/min. The antibody was diluted so as to obtain a series of concentrations, a 1:1 (Langmuir) binding model was used to fit the data.

Epitope mapping of anti-DLL4 antibodies were done on Octet. AntiDLL-4 antibodies C3. G6 and OMP21M18 were immobilized on AR2G sensor with amine-coupling kit, loaded rhDLL4, then ran different antibodies. Additional binding would indicate that the antibodies bind to different epitope.

Results: This example illustrates an additional binding registered by Octet, indicating that C3, C5 and G6 antibodies bind to an epitope of DLL-4 that is not occupied by OMP21M18.

Example 3

This example shows the blocking of DLL4 binding to Notch-1 by disclosed anti-DLL4-antibodies. Human DLL-4 is a type I transmembrane protein exclusively expressed in endothelial cells. DLL-4 is a ligand for the membrane bound Notch-1 receptor. Upon binding to Notch-1, DLL-4 activates Notch signaling pathway, which plays a major role in angiogenesis and tumor vascular development. Blocking of this interaction would inhibit Notch-1 function in cells. The blocking was first evaluated in an ELISA-based immunoassay (FIG. 4A). Briefly, rat recombinant Notch (5 μg/ml) was coated onto the wells of micro-titer plates at 4° C. overnight and the plate was then blocked with casein-PBS buffer. His-tagged-rhDLL-4 (4 μg/ml) was pre-incubated with the anti-DLL-4 antibodies for 30 min, then transferred to the Notch-coated plate and incubated for 0.5 hr with shaking. An HRP-conjugated anti-his-tag antibody was used to detect binding of rhDLL-4 to Notch-1.

In parallel, the ability of anti-DLL-4 antibodies to block the binding of soluble recombinant Notch-1 protein to DLL-4-expressing CHO-K1 cells was assessed by HTFC. CHO-DLL-4 cells were lifted with enzyme-free Cell Dissociation Buffer (GIBCO), and incubated in FACS buffer+ Azide with 20 μg/ml FITC-rhNotch-1 in the presence or absence of anti-DLL-4 antibodies at fixed (FIG. 4B) or increasing (FIG. 4C) concentrations. Data were analyzed by flow cytometry.

Results: FIG. 4A illustrates that 3 of the disclosed anti-DLL-4 antibodies (C3, C10 and G6) were as efficient as OMP21M18 at blocking the binding of DLL-4 to Notch-1. This assay was repeated in a cellular context (FIG. 4B), that confirms that C3, C10 and G6 are able to efficiently inhibit the interaction of human DLL-4 with both Human and Rat Notch-1. These three antibodies appear more efficient ($IC_{50}$ values ranging from 2 to 6 nM) than OMP21M18 (IC50=1.72 nM) (FIG. 4C).

Example 4

This example shows the effect of anti-DLL-4 antibodies on Notch-1 pathway activation. Upon binding by DLL-4, the Notch-1 intracellular domain (NICD) is cleaved and translocates to the nucleus to activate the expression of specific target genes. Here we show that anti-DLL-4 antibodies inhibit DLL-4-mediated Notch-1 pathway activation and modulate expression of Notch target genes in a breast cancer cell Line. MCF7 cells expressing Notch-1 were co-incubated for 24 hr with CHO cells either over-expressing Human DLL-4 (DLL-4) or not (No DLL-4). Cells were then harvested and total RNA was extracted with Trizol (Life Technology) according to manufacturer's recommendations. Gene expression was analyzed by RT-PCR using Promega's Access RT-PCR System kit, according to the Company's instructions. The forward and reverse primers were as follows: Notch-1 Forward CACTGTGGGCGGGTCC SEQ ID NO. 41, Notch-1 Reverse: GTITGTATTGGTTCGGCAC-CAT SEQ ID NO. 42, HEY-1 Forward: GGAGAGGCGC-CGCTGTAGTTA SEQ ID NO. 43, HEY-1 Reverse: CAAGGGCGTGCGCGTCAAAGTA, SEQ ID NO. 44 GAPDH Forward: GGACCTGACCTGCCGTCTAGAA, SEQ ID NO. 45 GAPDH Reverse: GGTGTCGCTGTT-GAAGTCAGAG SEQ ID NO. 46. PCR samples were run on a 3% agarose gel and bands intensities were quantified using Image Lab Software (BIORAD). Human GAPDH was used as a reference gene for normalization.

Results: FIG. 5 shows that the presence of DLL-4 stimulated Hey-1 and Notch-1 expression, and that anti-DLL-4 antibody C3 efficiently inhibited DLL-4 stimulation of Notch-1 target gene regulation.

Example 5

This example shows an in vitro cell proliferation assay illustrating the ability of the disclosed anti-DLL-4 antibodies to antagonize DLL-4-mediated growth inhibition of Human Umbilical Vein Endothelial Cells (HUVEC). Angiogenesis is a complex finely regulated process. DLL-4 inhibits VEGF-mediated endothelial cell proliferation, and is induced by VEGF as a negative feedback regulator, thus preventing overly extensive angiogenic sprouting. It was previously shown that inhibition of DLL-4 rendered endothelial cells hyperproliferative, causing defective cell fate specification or differentiation both in vitro and in vivo. Hence, blocking DLL-4 was shown to inhibit tumor growth in several tumor models. In this assay, low passage HUVEC cells were obtained from LONZA and cultured in EGM™-2 media (LONZA). One day prior to experiment, 96 well-plates were coated at 4° C. overnight with 0.1% Gelatin+2 μg/ml rHuDLL-4 (SinoBiologics) or 0.1% Bovine Serum Albumin (BSA, SIGMA). Then cells were lifted with Stem-Pro Accutase (Life Technology) and added to the plates at 5,000 cells/well in normal culture media, and returned for 3 days incubation at 37° C. Results were analyzed using a standard MTT assay.

Results: FIG. 6 shows that HUVEC proliferation was inhibited when cells were cultured on immobilized DLL-4, and that disclosed anti-DLL-4 antibodies (C3, C10 and G6) were capable of restoring HUVEC proliferation. This antagonism of DLL-4 function was as efficient, or more potent than Oncomed's OMP21M18 antibody.

TABLE 1

Human Anti-Dll-4 antibody sequences variable domain regions

| Clones | Heavy chain | Light chain |
|---|---|---|
| C3 | QVQLVQSGSELKKPGASVKVSCKAS GYTFTSYYMHWVRQVPGQGLEWMG IINPSGGSTSYAQKFQGRVTMTRDTS TSTVYMELSSLRSEDTAVYYCATDYY DSSGYVDFDYWGQGTLVTVSS SEQ ID No. 1 | QSVLTQPPSASGTPGQRVTISCSGSSSNIG SNTVNWYQQFPGTAPKLLIYRNNQRPSGV PDRFSGSKSGTSASLAISGLQSEDEADYY CAAWDDSPNGPVFGGGTKLTVL SEQ ID No. 2 |
| C5 | QVQLQQSGPGLVKPSQTLSLTCAISG DSVSSNSAAWNWIRQSPSRGFEWL GRTEYRSKWYNDYAVSVESRITINPD TSKNHFSLQLNSVTPEDTAVYYCARD GNTESEDYWGQGTLVTVSS SEQ ID NO. 3 | QSVVTQPPSVSAAPGQKVTISCSGGSSNI GNNYVSWYQQIPGTAPKLLIYDNNNRPSGI PDRFSGSKSGASATLGISGLQTGDEANYY CGAWDSTLSGYVFGTGTKLTVL SEQ ID NO. 4 |
| C10 | QVQLVESGAEVKKPGASVKVSCKAS GYTFTSYYMHWVRQAPGQGLEWMGII NPSGGSTSYAQKFQGRVTMTRDTST NTVYMELSSLRSEDTAVYYCARDVW GGYFDYWGQGTLVTVSS SEQ ID NO. 5 | QSVLTQPASVSGSPGQSITISCTGTSSDVG GYNYVSWYQQHPGKAPKLMIYDVTNRPS GVSNRFSGSKSGNTASLTISGLQAEDEAD YYCSSYTSSSTVIFGGGTKLTVL SEQ ID NO. 6 |
| G6 | EVQLVESGGSLVQPGGSLRLSCAAS GFTFSNGWMTWLRQAPGKGLEWVA TIKPDGSDTAYVESVKGRFTISRDNA KNLLYLQMDSLRGDDTAVYFCARDL AYNAFDIWGQGTMVTVSS SEQ ID NO. 7 | QSVLTQPPSASGTPGQRVTISCSGSSSNIG SNTVNWYQQLPGTAPKLLIYSNNQRPSGV PDRFSGSKSGTSASLAISGLQSEDEADYY CAAWDGSLNGYVFGTGTKLTVL SEQ ID NO. 8 |
| F11 | EVQLVESGAEVKKPGASVKVSCKAS GYTFTSYYMHWVRQAPGQGLEWMG IISPSGDSTSYAQKFQGRVTMTKDTS TSTVSMELSSLRSEDTAVYYCARDQ EGLRGSGYYGMDVWGQGTTVTVSS SEQ ID NO. 9 | SQPVLTQPASVSGSPGQSITISCTGTSSDI GDYNYVSWYQQHPGKAPKLMIYEVSKRPS GVPDRFSGSKSGNTASLTISGLQAEDEAD YYCYSYAGSYTYVFGTGTKLTV SEQ ID NO. 10 |
| D2 | QVQLVESGAEVKKPGASVKVSCKAS GYTFTTYFIHWVRQAPGQGLEWMGII NPSGGSTSYAQKFQGRVTMTRDTST STVYMELSSLRSEDTAVYYCAREFM ATGGFDYWGQGTLVTVSS SEQ ID NO. 11 | QPVLTQPASVSGSPGQSITIPCTGTRSDVG GYNFVSWYQQHPGKAPKLLIYDNNKRPSG IPGRFSGSKSGTSATLGITGLQTGDEADYY CGTWDDSLNVWVFGGGTKVTVL SEQ ID NO. 12 |
| E10 | EVQLVQSGAEVKKPGASVKVSCKAS GYSFMNYDVTWVRQAAQGLEWMG WMNPDSGNTGYADQFQGRITMTRD TSKSTAYMELTSLRSDDTAVYFCARA EVEVPGYYYKYGMDVWGQGTTVTV SS SEQ ID NO. 13 | AIRMTQSPSFLSASVGDRITITCRASQDISA YLAWYQQKPGTAPKVLIYAASTLQSGVPS RFSGSGSGTEFTLTISSLQPEDFATYYCQQ LYDYLPITFGPGTKVDIK SEQ ID NO. 14 |
| F12 | QVQLVQSGAEVKKPGESVIISCKSSG FTFTRTAIHWMRQAPGQSFEWVGWI RGSNGDTSYSQKFRDKVTVTADTFS STSYLALNRLTSEDTAVYYCAREHPT SWDPDFWGQGTLVTVSS SEQ ID NO. 15 | LPVLTQPRSVSGSPGQSVTISCTGTSSDV GGYNYVSWYQHHPGKAPKLMIYDVTKRPS GVPDRFSGSKSGNTASLTISGLQAEDEAD YYCSSYTSSSTPYVFGTGTKVTVL SEQ ID NO. 16 |
| E5 | QVQLQQSGPGLVQPSQTLSLTCVIS GDSVSNNNAAWTWIRQSPSRGLEW LGRTYYRSQWYSDYAVSVKSRMTIN PDTSKNQFSLQLNSLTPEDTAVYYCA REEVMDHDAFDIWGPGTMVTVSS SEQ ID NO. 17 | LPVLTQSPSASGTPGQRVTISCSGSTSNIG SNTVNWYQQFPGTAPKLLIYYNDQRPSGV PDRFSGSKSGTSASLAISGLQSEDEADYY CAAWDDRLYGRLFGGGTKLIVL SEQ ID NO. 18 |
| H2 | EVQLLESGGGLVQPGGSLRLSCAAS GFNVSKNYMSWVRQAPGKGLEWVS SMSSSSSYKYYADSVKGRFTISRDNA KNSLYLQMNSLRAEDTAVYYCAREN DREAFDIWGQGTMVTVSS SEQ ID NO. 19 | EIVMTQSPSSLSASVGDRVTITCRASQSISS YLNWYQQKPGKAPKLLIYAASSLQSGVPS RFSGSGSGTDFTLTISSLQPEDFATYYCQQ SYSTPLTFGQGTRLEIK SEQ ID NO. 20 |

TABLE 1-continued

Human Anti-D11-4 antibody sequences variable domain regions

| Clones | Heavy chain | Light chain |
|---|---|---|
| A1 | QVQLQQSGPGLVKPSQTLSLTCAISG<br>DSVSSNGVAWNWIRQSPSRGLEWL<br>GRTYFNSKWYNDYAVSVESRITINPD<br>TSKNQFSLQLNSVTPEDTAVYYCAR<br>GRVSAFDYWGQGTPVTVSS<br>SEQ ID NO. 21 | QPVLTQPASVSGSPGQSITISCTGTSNDVG<br>SYDLVSWYQQHPGKAPKLMTYDVSNRPS<br>GVSNRFSGAKSGNTASLTISGLQAEDEAD<br>YYCSSYTTSSTVVFGGGTKLTVL<br>SEQ ID NO. 22 |
| A2 | EVQLVQSGAEVKKPGASVKVSCKAS<br>GYTFTSDEINWVRQATGQGLEWLG<br>WMNPHSGNTGYAQKFQGRVTMTRN<br>TSISTADMELSSLTSDDTAVYYCARG<br>HYYESSGYFFYGMDVWGQGTTVTV<br>SS<br>SEQ ID NO. 23 | QPVLTQPASVSGSPGQSITISCTGTSSDVG<br>GYNYVSWFQQHPGKAPKLMIYDVNNRPS<br>GVSNRFSGSKSGNTASLTISGLQAEDGAD<br>YYCSSYTSSSTYVFGTGTKVTVL<br>SEQ ID NO. 24 |
| A11 | QVQLQQSGPGLVKPSQTLSLTCAISG<br>DSVSSNSAAWNWIRQSPSRGLEWL<br>GRTYYRSKWYNDYAVSVKSRITINPD<br>TSKNQFSLQLNSVTPEDTAVYYCARE<br>GDDYGDHFDYWGQGTLVTVSS<br>SEQ ID NO. 25 | QSVLTQPPSVSEAPRQGVTISCSGSRSNIG<br>NNPVSWYQQVPGKPPKLLIYFDDLLPSGV<br>SDRFSASKSGTSASLAISGLQSDDEADYFC<br>AAWDDSLNGRVFGGGTKLTVL<br>SEQ ID NO. 26 |
| C12 | EVQLLESGAEVKKPGASVKVSCKAS<br>GYTFTSYAMHWVRQAPGQRLEWLG<br>HINAANGNTKYSQKFQGRVTITRDTS<br>ASTAYMELSSLRSEDTAVYYCARAR<br>SGSYLVDYWGQGTLVTVSS<br>SEQ ID NO. 27 | YVLTQPPSASGTPGQRVTISCSGSNSNIGS<br>NAVNWYQHLPGTAPKLLIYSNNQRPSGVP<br>DRFSGSKSGTSASLAISGLQSEDESDYYCI<br>AWDGSLSGYVFGTGTKVTVL<br>SEQ ID NO. 28 |
| D9 | QVQLVESGAEVRKPGASVKVSCKAS<br>GYTFTDYAIHWVRQAPGQRLEWMG<br>WINAGNGNTKYSQKFQGRVTITRDT<br>SASTAYMELSSLRSEDAAVYYCARG<br>NGSGSYLVDYWGQGTLVTVSS<br>SEQ ID NO. 29 | QSVVTQPPSLSAAPGQRVSISCSGTSSNIG<br>KNYVSWYQQVPGTAPRLLIYDNNKRASGI<br>PARFSGSKSATSATLDIAGLQTGDEADYFC<br>ETWDSSLRAEIFGGGTKLTVL<br>SEQ ID NO. 30 |
| E3 | QVQLVESGAEVKKPGASVKVSCKAS<br>GYTFTSYPMHWVRQAPGQRLEWMG<br>WINAGNGDTKYSQKFQDRVTITSDTS<br>ASTAYMELSSLRSEDTAVYYCAKDYY<br>TSGTYQIDYWGQGTLVTVSS<br>SEQ ID NO. 31 | SYELMQPHSVSESPGKTVTISCTRSSGNIA<br>SNYVRWYQQRRDSAPTVVIFDDDQKPSG<br>VADRFSGSIDTSSNSASLTISGLNTDDEAA<br>YYCHSDESSTVIFGGRTKLTVL<br>SEQ ID NO. 32 |
| E6 | EVQLVQSGAEVKKPGASVKVSCKAS<br>GYTFTSYTMHWVRQAPGQRLEWMG<br>WINAGNGNTKYSQKFQGRVTITRDTF<br>ASTAYMELSSLRSEDTAVYYCARSR<br>YNSGGSLVDYWGQGTLVTVSS<br>SEQ ID NO. 33 | QSVVTQPPSVSAAPGQKVTISCSGSSSNIE<br>NNYVSWYQQLPGTAPKLLIYDNNKRPSGIP<br>DRFSGSKSGTSATLGITGLQTGDEADYYC<br>GTWDSSLSAEVFGTGTKVTVL<br>SEQ ID NO. 34 |
| F1 | QVQLVQSGAEVKKPGTSVKVSCKTS<br>GFPFTTYFFHWARQAPGQRPEWMG<br>WIHGGNGNTKYSQKFQGRVTITRDT<br>SASTAYMELSSLRSEDAAVYYCARG<br>NGSGSYLVDYWGQGTLVTVSS<br>SEQ ID NO. 35 | QAGLTQPPSASGSPGQPVTISCSGTSGDV<br>GGYDYVSWYQQHPGKAPKLIIYDVNKRPS<br>GVPDRFSGSKSGNTASLTVSGLQAEDEAD<br>YHCSSYAGSNNVIFGGGTKLTVL<br>SEQ ID NO. 36 |
| F6 | QVQLVESGAEVKKPGASVKVSCKAS<br>GYTFTNFFMHWVRQAPGQGLEWMG<br>VINPSGPGTTYPQKFQDRVTMTRDT<br>STSTVYMELSSLRSDDTAVYYCARDL<br>INSGWSGAFDIWGQGTMVTVSS<br>SEQ ID NO. 37 | QPVLTQPPSVSVAPGNTASITCGENNIGSK<br>SVHWYQQKPGQAPVLVIYYDSDRPSGIPE<br>RFSGSNSGNTATLTISRVEAGDEADYYCQ<br>VWDSSSDSWVFGGGTKVTVL<br>SEQ ID NO. 38 |
| F10 | QVQLVQSGAEVKEPGASVKVSCKTS<br>GFTFTQIYVHWVRQAPGQGLEWMG<br>LVRPSGSSRIYGQNFQGRVTLTRDTS<br>TSTVYMDLSSLTSEDTAVYYCVTDVA<br>GYGDGRVWGQGTLVTVSS<br>SEQ ID NO. 39 | QSVLTQPPSVSAAPGQKVTISCSGSSSNIA<br>NSYVSWYQQLPGTAPKLLIYDNNQRPSGIP<br>DRFSGSKSGTSATLGITGLQTGDEADYYC<br>GTWDSSLSAGVFGTGTKLTVL<br>SEQ ID NO. 40 |

We claim:

1. A method for blocking an interaction between Notch-1 and DLL-4, comprising administering an effective amount of an antibody that binds to a Delta-like 4 (DLL-4) epitope, the antibody comprising: a heavy chain variable domain sequence comprising SEQ ID NO. 1, SEQ ID NO. 5, or SEQ ID NO. 7; and a light chain variable domain sequence comprising SEQ ID NO. 2, SEQ ID NO. 6, or SEQ ID NO. 8.

2. The method of claim 1, wherein the antibody comprises a heavy chain/light chain variable domain sequence selected from the group consisting of SEQ ID NO. 1/SEQ ID NO. 2, SEQ ID NO. 5/SEQ ID NO. 6, and SEQ ID NO. 7/SEQ ID NO. 8.

3. The method of claim 1, wherein the antibody is selected from the group consisting of a Fab, a Fab', a F(ab')2, an Fv, a domain antibody (dAb), a single-chain antibody, a chimeric antibody, a diabody, a triabody, a tetrabody, a fully human antibody, a humanized antibody, and a chimeric antibody.

4. The method of claim 3, wherein the antibody is an IgG.

5. A method for blocking an interaction between Notch-1 and DLL-4, comprising administering an effective amount of an antibody Fab fragment that binds to a DLL-4, epitope, the Fab fragment comprising: a heavy chain variable domain sequence comprising SEQ ID NO. 1, SEQ ID NO. 5, or SEQ ID NO. 7, and a light chain variable domain sequence comprising SEQ ID NO. 2, SEQ ID NO. 6, or SEQ ID NO. 8.

6. The method of claim 5, wherein the Fab fragment comprises a heavy chain/light chain variable domain sequence selected from the group consisting of SEQ ID NO. 1/SEQ ID NO. 2, SEQ ID NO. 5/SEQ ID NO. 6, and SEQ ID NO. 7/SEQ ID NO. 8.

7. A method for blocking an interaction between Notch-1 and DLL-4, comprising administering an effective amount of a single-chain antibody, or fragment thereof, that binds to a DLL-4 epitope, the single-chain antibody comprising: a heavy chain variable domain sequence comprising SEQ ID NO. 1, SEQ ID NO. 5, or SEQ ID NO. 7, and a light chain variable domain sequence comprising SEQ ID NO. 2, SEQ ID NO. 6, or SEQ ID NO. 8, wherein the heavy chain variable domain and the light chain variable domain are connected by a peptide linker.

8. The method of claim 7, wherein the single-chain antibody, or fragment thereof, comprises a heavy chain/light chain variable domain sequence selected from the group consisting of SEQ ID NO. 1/SEQ ID NO. 2, SEQ ID NO. 5/SEQ ID NO. 6, and SEQ ID NO. 7/SEQ ID NO. 8.

9. A method for blocking an interaction between Notch-1 and DLL-4, comprising administering an effective amount of an antibody that binds to a DLL-4 epitope, the antibody comprising:
   (a) a heavy chain variable domain comprising CDR1, CDR2 and CDR3 region amino acid sequences set forth in SEQ ID NO. 1, 5, or 7; and
   (b) a light chain variable domain comprising CDR1, CDR2 and CDR3 region amino acid sequences set forth in SEQ ID NO. 2, 6, or 8.

10. The method of claim 9, wherein the antibody comprises:
   (a) a heavy chain variable domain comprising CDR1, CDR2 and CDR3 region amino acid sequences set forth in SEQ ID NO. 1; and
   (b) a light chain variable domain comprising CDR1, CDR2 and CDR3 region amino acid sequences set forth in SEQ ID NO. 2.

11. The method of claim 9, wherein the antibody comprises:
(a) a heavy chain variable domain comprising CDR1, CDR2 and CDR3 region amino acid sequences set forth in SEQ ID NO. 5; and
(b) a light chain variable domain comprising CDR1, CDR2 and CDR3 region amino acid sequences set forth in SEQ ID NO. 6.

12. The method of claim 9, wherein the antibody comprises:
(a) a heavy chain variable domain comprising CDR1, CDR2 and CDR3 region amino acid sequences set forth in SEQ ID NO. 7; and
(b) a light chain variable domain comprising CDR1, CDR2 and CDR3 region amino acid sequences set forth in SEQ ID NO. 8.

13. The method of claim 9, wherein the antibody is selected from the group consisting of a Fab, a Fab', a F(ab')2, an Fv, a domain antibody (dAb), a single-chain antibody, a chimeric antibody, a diabody, a triabody, a tetrabody, a fully human antibody, a humanized antibody, and a chimeric antibody.

14. The method of claim 13, wherein the antibody is a Fab.

15. The method of claim 13, wherein the antibody is a single-chain antibody.

16. The method of claim 13, wherein the antibody, wherein the antibody is an IgG.

17. A method for blocking an interaction between Notch-1 and DLL-4, comprising administering an effective amount of an antibody that binds to a DLL-4 epitope, the antibody comprising a heavy chain variable domain comprising an amino acid sequence selected from the group consisting of SEQ ID NO. 1, 5, and 7, and further comprising a light chain.

18. The method of claim 17, wherein the heavy chain variable domain comprises the amino acid sequence set forth in SEQ ID NO. 1.

19. The method of claim 17, wherein the heavy chain variable domain comprises the amino acid sequence set forth in SEQ ID NO. 5.

20. The method of claim 17, wherein the heavy chain variable domain comprises the amino acid sequence set forth in SEQ ID NO. 7.

21. A method for blocking an interaction between Notch-1 and DLL-4, comprising administering an effective amount of an antibody that binds to a DLL-4 epitope, the antibody comprising a light chain variable domain comprising an amino acid sequence selected from the group consisting of SEQ ID NO. 2, 6, and 8, and further comprising a heavy chain.

22. The method of claim 21, wherein the light chain variable domain comprises the amino acid sequence set forth in SEQ ID NO. 2.

23. The method of claim 21, wherein the light chain variable domain comprises the amino acid sequence set forth in SEQ ID NO. 6.

24. The method of claim 21, wherein the light chain variable domain comprises the amino acid sequence set forth in SEQ ID NO. 8.

25. A method for blocking an interaction between Notch-1 and DLL-4, comprising administering an effective amount of an antibody that binds to a DLL-4 epitope, wherein the antibody comprises a heavy chain/light chain variable domain sequence selected from the group consisting of SEQ ID NO. 1/SEQ ID NO. 2, SEQ ID NO. 5/SEQ ID NO. 6, and SEQ ID NO. 7/SEQ ID NO. 8.

26. The method of claim 25, wherein the the heavy chain/light chain variable domain sequence is SEQ ID NO. 1/SEQ ID NO. 2.

27. The method of claim 25, wherein the the heavy chain/light chain variable domain sequence is SEQ ID NO. 5/SEQ ID NO. 6.

28. The method of claim 25, wherein the the heavy chain/light chain variable domain sequence is SEQ ID NO. 7/SEQ ID NO. 8.

* * * * *

UNITED STATES PATENT AND TRADEMARK OFFICE
CERTIFICATE OF CORRECTION

PATENT NO. : 10,717,779 B2  
APPLICATION NO. : 16/241828  
DATED : July 21, 2020  
INVENTOR(S) : Edwige Gros et al.

Page 1 of 1

It is certified that error appears in the above-identified patent and that said Letters Patent is hereby corrected as shown below:

On the Title Page

Item (54), Line 4:  
Delete "DDL-4" and insert --DLL-4--

In the Specification

Column 1, Line 4:  
Delete "DDL-4" and insert --DLL-4--

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*